(12) United States Patent
Bruno

(10) Patent No.: US 10,925,533 B2
(45) Date of Patent: *Feb. 23, 2021

(54) SYSTEMS AND METHODS FOR DETERMINING HUMAN PERFORMANCE CAPACITY AND UTILITY OF A PERSON-UTILIZED DEVICE

(71) Applicant: Jeff Scott Bruno, San Luis Obispo, CA (US)

(72) Inventor: Jeff Scott Bruno, San Luis Obispo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/832,206

(22) Filed: Mar. 27, 2020

(65) Prior Publication Data
US 2020/0265942 A1 Aug. 20, 2020

Related U.S. Application Data

(63) Continuation of application No. 15/280,797, filed on Sep. 29, 2016, now Pat. No. 10,643,745.

(60) Provisional application No. 62/234,566, filed on Sep. 29, 2015.

(51) Int. Cl.
| | |
|---|---|
| *A61B 5/16* | (2006.01) |
| *G16H 20/70* | (2018.01) |
| *G16H 50/20* | (2018.01) |
| *G16H 20/30* | (2018.01) |
| *A61B 5/00* | (2006.01) |
| *A61N 1/36* | (2006.01) |

(Continued)

(52) U.S. Cl.
CPC .............. *A61B 5/16* (2013.01); *G16H 20/30* (2018.01); *G16H 20/70* (2018.01); *G16H 50/20* (2018.01); *A61B 5/0476* (2013.01); *A61B 5/4076* (2013.01); *A61B 5/4884* (2013.01); *A61N 1/0456* (2013.01); *A61N 1/36025* (2013.01)

(58) Field of Classification Search
CPC ....... A61B 5/16; A61B 5/4884; A61B 5/0476; A61B 5/4076; G16H 20/70; G16H 50/20; A61N 1/0456; A61N 1/36025
See application file for complete search history.

(56) References Cited

U.S. PATENT DOCUMENTS

| | | |
|---|---|---|
| 4,683,891 A | 8/1987 | Cornellier |
| 5,515,858 A | 5/1996 | Myllymaeki |
| 5,724,987 A | 3/1998 | Gevins |

(Continued)

OTHER PUBLICATIONS

Allen; "Occupational Therapy Expert Opinions on Work Capacity: A Grounded Theory", Doctorial Dissertation; School of Health and Rehabilitation Sciences; University of Queensland; Jul. 2005; 490 pages.

(Continued)

*Primary Examiner* — Malina D. Blaise
(74) *Attorney, Agent, or Firm* — Fitch, Even, Tabin & Flannery LLP

(57) ABSTRACT

A system and method of determining human performance capacity, and of determining the utility of a given biomedical intervention and/or neurotechnology device to characterize, to predict, and to influence human performance capacity, via analysis and interpretation of psychophysiological biomarkers of cognitive workload and functioning, assistive-technology/external support dependence, and compensatory behavior during performance of ecologically-valid standardized work samples.

27 Claims, 7 Drawing Sheets

(51) Int. Cl.
*A61B 5/0476* (2006.01)
*A61N 1/04* (2006.01)

(56) References Cited

U.S. PATENT DOCUMENTS

| | | | |
|---|---|---|---|
| 6,309,342 B1 | 10/2001 | Blazey | |
| 6,348,867 B1 | 2/2002 | Myllymaeki | |
| 6,390,979 B1* | 5/2002 | Njemanze | A61B 5/16 600/438 |
| 6,416,472 B1 | 7/2002 | Cady | |
| 6,527,715 B2 | 3/2003 | Balkin | |
| 6,726,624 B2 | 4/2004 | Keirsbilck | |
| 7,423,526 B2 | 9/2008 | Despotis | |
| 7,598,878 B2 | 10/2009 | Goldreich | |
| 7,751,889 B1 | 7/2010 | Schecter | |
| 8,135,472 B2 | 3/2012 | Fowler | |
| 9,179,847 B2 | 11/2015 | Eggenberger | |
| 9,251,716 B2 | 2/2016 | Drane | |
| 9,737,255 B2* | 8/2017 | Chen | A61B 5/4803 |
| 2004/0037236 A1* | 2/2004 | Massey | A61B 5/18 370/277 |
| 2005/0283204 A1 | 12/2005 | Buhlmann | |
| 2006/0139312 A1 | 6/2006 | Sinclair, II | |
| 2007/0016034 A1 | 1/2007 | Donaldson | |
| 2008/0120264 A1 | 5/2008 | Lee | |
| 2009/0069707 A1 | 3/2009 | Sandford | |
| 2009/0319459 A1 | 12/2009 | Breazeal | |
| 2010/0076274 A1 | 3/2010 | Severson | |
| 2010/0138026 A1* | 6/2010 | Kaushal | G05B 13/0265 700/104 |
| 2010/0217097 A1 | 8/2010 | Chen | |
| 2010/0292545 A1 | 11/2010 | Berka | |
| 2011/0004412 A1 | 1/2011 | Shahaf | |
| 2011/0105281 A1 | 5/2011 | Jerichow | |
| 2011/0183305 A1 | 7/2011 | Orbach | |
| 2011/0207099 A1* | 8/2011 | Chen | A61B 5/4803 434/236 |
| 2012/0130266 A1 | 5/2012 | Mathan | |
| 2012/0329027 A1 | 12/2012 | Lewolt | |
| 2012/0330869 A1 | 12/2012 | Durham | |
| 2014/0223462 A1* | 8/2014 | Aimone | G16H 40/67 725/10 |
| 2014/0266737 A1 | 9/2014 | Caldwell | |
| 2014/0279746 A1 | 9/2014 | De Bruin | |
| 2014/0330576 A1 | 11/2014 | Bauer | |
| 2014/0335480 A1 | 11/2014 | Asenjo | |
| 2015/0018630 A1 | 1/2015 | Fotuhi | |
| 2015/0025917 A1 | 1/2015 | Stempora | |
| 2016/0007915 A1 | 1/2016 | Berka | |
| 2016/0015280 A1 | 1/2016 | Hyde | |
| 2017/0003793 A1 | 1/2017 | Gao | |
| 2017/0156662 A1 | 6/2017 | Goodall | |
| 2018/0356846 A1 | 12/2018 | Sharpe | |
| 2019/0304329 A1* | 10/2019 | Webb | G09B 3/02 |

OTHER PUBLICATIONS

American Medical Association (AMA); "Guide to the Evaluation of Functional Ability"; 2009; Chapter 19, pp. 358-359; Chapter 22, pp. 430-431.
American Medical Association (AMA); "Guide to the Evaluation of Permanent Impairment"; 2008, Chapter 1, p. 6; Chapter 14, p. 356.
Badley; "Enhancing the Conceptual Clarity of the Activity and Participation Components of the International Classification of Functioning, Disability, and Health"; Social Science & Medicine 66; Mar. 7, 2008; pp. 2335-2345.
Badley; "The Genesis of Handicap: Definition, Models of Disablement, and the Role of External Factors"; Disability and Rehabilitation, vol. 17, No. 2; 1995; pp. 53-62.
Baum et al.; "Reliability, Validity, and Clinical Utility of the Executive Function Performance Test: A Measure of Executive Function in a Sample of People with Stroke"; American Journal of Occupational Therapy, vol. 62, No. 4; Jul./Aug. 2008; pp. 446-455.

Bjorkdahl; "The Return to Work After a Neuropsychological Programme and the Prognostic Factors for Success"; Brain Injury 24(9); Aug. 2010; pp. 1061-1069.
Brokaw et al.; "Sitting and Standing Tolerance in Patients with Chronic Back Pain: Comparison Between Physician Prediction and Covert Observation"; Archives of Physical Medicine and Rehabilitation; vol. 85; May 2004; pp. 837-839.
Brouwer et al; "Comparing Self-Report, Clinical Examination and Functional Testing in the Assessment of Work-Related Limitations in Patients with Chronic Low Back Pain"; Disability and Rehabilitation; Oct. 2005; pp. 999-1005.
Bruno; U.S. Appl. No. 15/280,797, filed Sep. 29, 2016.
Butler et al; "Impairment Ratings for Back Claims are Poor Predictors of Wage Loss"; Journal of Occupational Rehabilitation, vol. 10, No. 2; 2000; pp. 153-168.
Chan et al; "Assessment of Executive Functions: Review of Instruments and Indentification of Critical Issues"; Archives of Clinical Neuropsychology, 23; Aug. 28, 2007; pp. 201-206.
Chaytor et al; "Improving the Ecological Validity of Executive Functioning Assessment"; Archives of Clinical Neuropsychology 21; 2006; pp. 217-227.
Farzad et al; "Does Disability Correlate with Impairment after Hand Injury?"; Clinical Orthopedics and Related Research, vol. 473, No. 11; Mar. 5, 2015; pp. 3470-3476.
Farzad et al; "Exploring the Relationship Between Impairment Rating by AMA Guide and Activity and Participation Based on ICF in the Patients with Hand Injuries"; Journal of Hand and Microsurgery; Aug. 12, 2015.
Faust; "Forensic Neuropsychology: The Art of Practicing a Science that Does Not Yet Exist"; Neuropsychology Review; vol. 2, No. 3; 1991; pp. 205-231.
Guilmette; "Prediction of Vocational Functioning From Neuropsychological Data"; Handbook of Complex Occupational Disability Claims; 2005; pp. 303-314.
Hazard et al; "Chronic Low Back Pain: The Relationship Between Patient Satisfaction and Pain, Impairment, and Disability Outcomes"; Spine, vol. 18, No. 8; 1994; pp. 881-887.
Hazard et al; "Functional Restoration With Behavioral Support: A One-Year Prospective Study of Patients With Chronic Low-Back Pain"; Spine, vol. 14, No. 2 ; 1989; pp. 157-161.
Jette et al; "Conceptual Issues in the Measurement of Work Disability" Survey Measurement of Work Disability: Summary of a Workshop; Institute of Medicine and National Research Council; National Academy of Sciences; 2000; retrieved Feb. 10, 2004 from http://books.nap.edu/html/work_disability/ch2.html; Chapter 2, pp. 4-27.
LeBlanc et al; "A Comparison of Neuropsychological and Situational Assessment for Predicting Employability After Closed Head Injury"; Journal of Head Trauma Rehabilitation 15(4); Jun. 26, 2000; pp. 1022-1040.
Lezak et al; "Executive Functions and Motor Performance" Neuropsychological Assessment Fourth Edition; Oxford University Press; 2004; pp. 611-612.
Mandell et al; "Isokinetic Trunk Strength and Lifting Strength Measures: Differences and Similarities Between Low-Back-Injured and Noninjured Workers"; Spine, vol. 18, No. 16 ; 1993; pp. 2491-2501.
Matheson et al; "Improving the Validity of the Impairment Evaluation Process: A Proposed Theoretical Framework"; Journal of Occupational Rehabilitation, vol. 10, No. 4; 2000; pp. 311-320.
Matheson; "The Functional Capacity Evaluation"; Disability Evaluation, 2nd Edition; 2003; 35 pages.
Milhous et al; "Determinants of Vocational Disability in Patients with Low Back Pain" Archives Physical Medicine Rehabilitation, vol. 70; Aug., 1989; pp. 589-593.
Million et al; "Assessment of the Progress of the Backpain Patient"; Spine, vol. 7, No. 3; 1982; pp. 204-212.
Mooney; "Impairment, Disability, and Handicap"; Clinical Orthopedics and Related Research, No. 221; Aug. 1987; pp. 14-25.
Newton et al; "Trunk Strength Testing with Iso-Machines Part I: Review of a Decade of Scientific Evidence"; Spine, vol. 18, No. 7; 1993; pp. 801-811.

(56) References Cited

OTHER PUBLICATIONS

Ponsford et al; "Traumatic Brain Injury: Rehabilitation for Everyday Adaptive Living"; Psychology Press; 2013; pp. 89 and 91.
Reville et al; "Comparing Severity of Impairment for Different Permanent Upper Extremity Musculoskeletal Injuries"; Journal of Occupational Rehabilitation, vol. 12, No. 3; Sep. 2002; pp. 205-221.
Sbordone; "Limitations of Neuropsychological Testing Predict the Cognitive and Behavioral Functioning of Persons with Brain Injury in Real-World Settings"; Neurorehabilitation (16); 2001; pp. 199-201.
Spikeman et al: "Recovery Versus Retest Effects in Attention after Closed Head Injury"; Journal of Clinical and Experimental Neuropsychology vol. 21, No. 5; 1999; pp. 585-605.
Todd: "Predetermined Time Standards: Their Application in Workshop Settings"; Archives of Physical Medicine and Rehabilitation; May 1979; Abstract only (article no longer available).
Torgerson et al; "Comparative Roentgenographic Study of the Asymptomatic and Symptomatic Lumbar Spine";The Journal of Bone and Joint Surgery, vol. 58-A, No. 6; Sep. 1976; pp. 850-853.
USPTO; Advisory Action issued in U.S. Appl. No. 15/280,797 dated Mar. 18, 2019.
USPTO; Examiner Interview Summary issued in U.S. Appl. No. 15/280,797 dated Jul. 24, 2018.
USPTO; Final Office Action issued in U.S. Appl. No. 15/280,797 dated Jan. 9, 2019.
USPTO; Non-Final Office Action issued in U.S. Appl. No. 15/280,797 dated May 9, 2018.
USPTO; Notice of Allowance issued in U.S. Appl. No. 15/280,797 dated Jan. 7, 2020.
Van Oosterom et al; "Impairment and Disability After Severe Hand Injuries with Multiple Phalangeal Fractures"; Journal of Hand Surgery, vol. 32A, No. 1; Jan. 2007; pp. 91-95.
Waddell et al; "Assessment of Severity in Low-Back Disorders"; Spine, vol. 9, No. 2; 1984; pp. 204-208.
Waddell et al; "Objective Clinical Evaluation of Physical Impairment in Chronic Low Back Pain"; Spine, vol. 17, No. 6; 1992; pp. 617-628.
Wind et al; "Effect of Functional Capacity Evaluation Information on the Judgment of Physicians about Physical Work Ability in the Context of Disability Claims"; International Archives of Occupational and Environmental Health, vol. 82; 2009; pp. 1087-1096.
Wolf et al; "Initial Development of a Work-Related Assessment of Dysexecutive Syndrome: The Complex Task Performance Assessment"; Work 31; 2008; pp. 221-228.
World Health Organization; "Towards a Common Language for Functioning, Disability and Health ICF";2002; 23 pages.

\* cited by examiner

| Comparison Type | Construct | Entities Compared | Mathematical Description For Score |
|---|---|---|---|
| Absolute Performance | Performance | Person vs. Work Sample | Percentage: based on Methods-Time Measurement (MTM) performance standard; Criterion-referenced |
| Relative Performance | Performance | Person vs. Person | Standard psychometrics; Norm-referenced |
| Relative Effort | Effort | Person vs. Person | Standard psychometrics; Norm-referenced |
| Absolute Efficiency | Performance and Effort | Person vs. Self | Ratio |
| Relative Efficiency | Performance and Effort | Person vs. Person | Standard psychometrics; Norm-referenced |
| Resource Efficiency | Performance, Effort, Augmentation, and Mitigation | Person vs. Self; Person vs. Person | Person vs. Self: Nominal, ordinal, interval, and ratio, and/or standard psychometrics<br>Person vs. Person: Standard psychometrics; Norm-referenced |
| Behavioral Efficiency | Performance, Effort, and Compensation | Person vs. Self Person vs. Person | Person vs. Self: Nominal, ordinal, interval, and ratio, and/or standard psychometrics<br>Person vs. Person: Standard psychometrics; Norm-referenced |

300 — Absolute Performance
302 — Relative Performance
304 — Relative Effort
306 — Absolute Efficiency
308 — Relative Efficiency
310 — Resource Efficiency
312 — Behavioral Efficiency

FIG. 3

|   | Subject A, Device X | Subject B, Device X |
|---|---|---|
| Absolute Performance | Methods-Time Measurement: 77 (entry level) | Methods-Time Measurement: 75 (entry level) |
| Relative Performance | Standard Score: 113; Percentile: 81st | Standard Score: 91; Percentile: 27th |
| Relative Effort | Standard Score: 96; Percentile: 40th | Standard Score: 103; Percentile: 58th |
| Absolute Efficiency | 1.25 | 1.75 |
| Relative Efficiency | Standard Score: 80; Percentile: 9th | Standard Score: 117; Percentile: 87th |
| Resource Efficiency | Standard Score: 76; Percentile: 5th | Standard Score: 130; Percentile: 98th |
| Behavioral Efficiency | Standard Score: 88; Percentile: 21st | Standard Score: 112; Percentile: 79th |

FIG. 6

| TOTAL COMPOSITE SCORE | |
|---|---|
| Subject A, Device X | Subject B, Device X |
| MTM: 77 (entry level) | MTM: 75 (entry level) |
| Absolute Efficiency: 1.25 | Absolute Efficiency: 1.75 |
| Total Standard Score: 86; Percentile: 18th | Total Standard Score: 115; Percentile: 84th |

FIG. 7

|  | Subject A, Device X (800) | Subject A, Device Y (802) |
|---|---|---|
| Absolute Performance (402) | Methods-Time Measurement: 77 (entry level) | Methods-Time Measurement: 75 (entry level) |
| Relative Performance (404) | Standard Score: 113; Percentile: 81st | Standard Score: 91; Percentile: 27th |
| Relative Effort (406) | Standard Score: 96; Percentile: 40th | Standard Score: 103; Percentile: 58th |
| Absolute Efficiency (408) | 1.25 | 1.75 |
| Relative Efficiency (410) | Standard Score: 80; Percentile: 9th | Standard Score: 117; Percentile: 87th |
| Resource Efficiency (412) | Standard Score: 76; Percentile: 5th | Standard Score: 130; Percentile: 98th |
| Behavioral Efficiency (414) | Standard Score: 88; Percentile: 21st | Standard Score: 112; Percentile: 79th |

FIG. 8

| TOTAL COMPOSITE SCORE | |
|---|---|
| Subject A, Device X (900) | Subject A, Device Y (902) |
| MTM: 77 (entry level) | MTM: 75 (entry level) |
| Absolute Efficiency: 1.25 | Absolute Efficiency: 1.75 |
| Total Standard Score: 86; Percentile: 18th | Total Standard Score: 115; Percentile: 84th |

FIG. 9

SYSTEMS AND METHODS FOR DETERMINING HUMAN PERFORMANCE CAPACITY AND UTILITY OF A PERSON-UTILIZED DEVICE

This application is a continuation of U.S. application Ser. No. 15/280,797, filed Sep. 29, 2016, entitled SYSTEMS AND METHODS FOR DETERMINING HUMAN PERFORMANCE CAPACITY AND UTILITY OF A BIOMEDICAL INTERVENTION/NEUROTECHNOLOGY DEVICE, which in turn claims the benefit of U.S. Provisional Application No. 62/234,566, filed Sep. 29, 2015, entitled SYSTEM AND METHOD OF DETERMINING HUMAN PERFORMANCE CAPACITY, both of which are incorporated in their entirety herein by reference.

BACKGROUND OF THE INVENTION

1. Field of the Invention

The present invention relates generally to human performance capacity, and more specifically to modification of human performance capacity using assistive technologies.

2. Discussion of the Related Art

Human performance capacity, also known as functional capacity, is the ability to perform goal-directed real-world activities in a context representative of everyday life. Neurotechnology, also known as brain-based biomedical technology, is the field of study devoted to understanding as well as to influencing the brain and/or behavior.

The present invention in accordance with various embodiments relates to the assessment of human performance capacity during reciprocal interactions with neurotechnology, as opposed to using neurotechnology to assess a person's condition for the purpose of medical diagnosis or other goal not associated with functional behavior in naturalistic settings. Although neurocognitive functioning can influence human performance capacity, no identifiable threshold of neurocognitive functioning has been established for making determinations regarding a person's ability or inability to perform goal-directed real-world activities, regardless of whether or not traditional paper-and-pencil neuropsychological tests (indirect measures of neuronal activity) or whether or not neurophysiological measures (direct measures of neuronal activity) are used. In fact, unless a person is found to be grossly and obviously incapacitated, regardless of diagnosis or of impairment rating, existing assessment methodologies are insufficient for characterizing, predicting, or influencing human performance capacity, particularly regarding a person's ability to perform activities requiring higher-level cognition, such as instrumental activities of daily living and work. Additionally, although existing performance-based assessments of functional behavior, such as the work samples comprising a cognitive functional capacity evaluation, provide a sound determination of a person's ability or inability to perform goal-directed real-world activities, no objective measurement of an individual's biological and/or neurological condition related to motivation, emotional state, fatigue, use of psychoactive substances, cognitive workload/cognitive effort exerted, reliance on compensatory behaviors (where compensatory behaviors as known in the art are psychological or performance strategies employed in order to cover up or minimize real or imagined deficiencies and/or personal, physical, cognitive, emotional, sensory, or functional limitations), or reliance on external-supports/assistive-technology such as software or invasive/non-invasive brain/biomedical supports is provided.

Approaches described in the prior art are not designed to and are incapable of assessing human performance capacity or the impact of a given neurotechnology device on human performance capacity. For example, U.S. Patent Application Publication No. 2010/0292545, published Nov. 18, 2010, describes a system and method of psychophysiological data collection and measurement for the purposes of assessing a person's general condition (cognitive and emotional state) as well as for establishing a medical diagnosis. Although the data collected may be generally implicated in the performance of real-world activities, no method of categorizing the data by relevance to functional abilities is established, and no method of situated (context-specific) data interpretation or application is provided. Additionally, no system or method of assessing the efficiency of a person's performance is provided, such as would be obtained by considering the degree and/or frequency of a person's usage of assistive-technology/external-supports and/or compensatory strategies in order to achieve a given performance score. Furthermore, with a methodology limited to a simple comparison of one person's profile as compared to a plurality of subjects, and with the data collected only during a person's performance of computerized assessments of discrete, circumscribed cognitive abilities, rather than during a person's performance of ecologically-valid standardized work samples, human performance capacity cannot be assessed. Finally, as no system or method of integrating biological, assistive-technology, behavioral, and performance-based data sets is provided, neither human performance capacity nor the utility of a given biomedical intervention or neurotechnology device for characterizing, predicting, or influencing human performance capacity can be assessed.

U.S. Pat. No. 6,416,472, issued Jul. 9, 2002, describes a system and method of assessing a person's cognitive efficiency via administration of standardized tests of cognitive ability without consideration of the mental effort exerted; however, by definition, efficiency is a measure of the performance obtained versus the investment or usage of resources (cognitive effort, assistive-technology/external-supports, compensatory behavior) in order to achieve said performance, but such data are not collected or analyzed. Additionally, as above, the data are collected only during a person's performance of computerized assessments of discrete, circumscribed cognitive abilities, rather than during a person's performance of ecologically-valid standardized work samples. Therefore, with the system and method described in the '472 patent neither human performance capacity nor the utility of a given biomedical intervention or neurotechnology device for characterizing, predicting, or influencing human performance capacity can be assessed.

U.S. Patent Application Publication No. 2010/0217097, published Aug. 26, 2010, describes a system and method of indirectly measuring only cognitive load via recoding of behavioral patterns and/or anomalies without consideration of rate and/or quality of activity performance. Additionally, no system or method of assessing the degree and/or frequency of a person's usage of assistive-technology/external-supports and/or compensatory strategies in order to achieve a given performance score is provided. Furthermore, as above, no ecologically-valid standardized work samples are performed; therefore, neither human performance capacity nor the utility of a given biomedical intervention or neurotechnology device for characterizing, predicting, or influencing human performance capacity can be assessed.

U.S. Patent Application Publication No. 2012/0130266, published May 24, 2012, describes a system and method of estimating cognitive efficacy (a term contained within the publication) based on values of mental effort exertion during a person's performance of a plurality of tasks. Baseline values of effort collected at an earlier date are compared to subsequent values collected at a later date; based on any changes in the data, a value of cognitive efficacy is estimated. With only intrapersonal comparisons, no system or method of contextualizing the significance of one person's effort score as compared to the effort score of appropriately-matched peers is provided. Additionally, the rate and/or quality of activity performance, the value of performance versus effort, and the degree and/or frequency of a person's usage of assistive-technology/external-supports and/or compensatory strategies are not considered. As no system or method of categorizing the data by comparison to appropriately-matched peers, of categorizing the data by relevance to a plurality of tasks, or of categorizing the data by efficiency is established, neither human performance capacity nor the utility of a given biomedical intervention or neurotechnology device for characterizing, predicting, or influencing human performance capacity can be assessed.

Finally, U.S. Pat. No. 6,527,715, issued Mar. 4, 2003, describes a system and method of predicting impaired performance on a cognitive task based on information regarding a person's daily activities and sleep/wake cycles, particularly for tasks during which brain areas most affected by sleep deprivation are utilized. Given that the system and method does not collect any empirical data regarding a person's actual performance of any task for which a person's performance capacity is being predicted, and given that the rate and/or quality of activity performance, the value of performance versus effort, and the degree and/or frequency of a person's usage of assistive-technology/external-supports and/or compensatory strategies are not considered, neither human performance capacity nor the utility of a given biomedical intervention or neurotechnology device for characterizing, predicting, or influencing human performance capacity can be assessed.

At present, no system or method of characterizing, predicting, or influencing human performance capacity during interactive usage of neurotechnology exists. Likewise, no system or method of determining the efficacy or the effectiveness, or the recommendations for use, of a given biomedical intervention or neurotechnology device to characterize, to predict, or to influence human performance capacity exists. Accordingly, what is needed is a system and method of integrating biological, assistive-technology, behavioral, and performance-based data sets, including direct measures of neuronal activity with direct measures of goal-directed real-world activity performance, collected simultaneously and in real time, in order to provide a comprehensive assessment of both human performance capacity and of the utility of a given biomedical intervention and/or neurotechnology device.

SUMMARY OF THE INVENTION

Several embodiments of the invention advantageously address the needs above as well as other needs by providing a method for adjusting a neurotechnology device comprising: providing a physical assessment sensor; generating data measuring performance, using the physical assessment sensor, of a person during a work sample, wherein the person interacts with at least one work sample object during the work sample; generating data measuring cognitive workload, using the physical assessment sensor, of the person during the work sample; generating one or more data sets as a function of the data measuring the performance, and data measuring the cognitive workload, the one or more data sets comprising an absolute efficiency data set indicating a cognitive effort exerted in order to achieve a given performance score; generating a composite score as a function of the one or more data sets; generating a profile of the person's work capacity, the profile including one or more of an expectation of the person's work rate, an expectation of the person's work quality, and the composite score; and adjusting the neurotechnology device as a function of the profile having been generated.

In another embodiment, the invention can be characterized as an apparatus for adjusting a neurotechnology device comprising: a physical assessment sensor; a performance measuring system, wherein the performance measuring system measures performance of a person while interacting with the physical assessment sensor during a work sample, wherein the person interacts with at least one work sample object during the work sample; a cognitive workload measuring system, wherein the cognitive workload measuring system measures a cognitive workload of the person while interacting with the physical assessment sensor during the work sample; a database, wherein the database compiles one or more data sets as a function of the performance, and the cognitive workload, the one or more data sets comprising an Absolute Efficiency data set; a composite score generator, wherein the composite score generator generates a composite score as a function of the one or more data sets; and a profile generator, wherein the profile generator generates a profile of the person's work capacity, the profile including one or more of an expectation of the person's work rate, an expectation of the person's work quality and a score determined from at least one of the one or more data sets, wherein the neurotechnology device is adjusted as a function of the profile having been generated.

BRIEF DESCRIPTION OF THE DRAWINGS

The above and other aspects, features and advantages of several embodiments of the present invention will be more apparent from the following more particular description thereof, presented in conjunction with the following drawings.

FIG. 3 is a table detailing the analysis of analyzed data sets of a data analysis and interpretation step of FIG. 1.

FIG. 6 is a table including an exemplary subject A profile and an exemplary subject B profile for a first analysis comparing two subjects in accordance with an embodiment of the present invention.

FIG. 7 is a table including an exemplary subject A composite profile and an exemplary subject B composite profile for the first analysis.

FIG. 8 is a table including an exemplary device X profile and an exemplary device Y profile for a second analysis comparing two devices in accordance with another embodiment of the present invention.

FIG. 9 is a table including an exemplary device X composite profile and an exemplary device Y composite profile for the second analysis.

Figure 1:
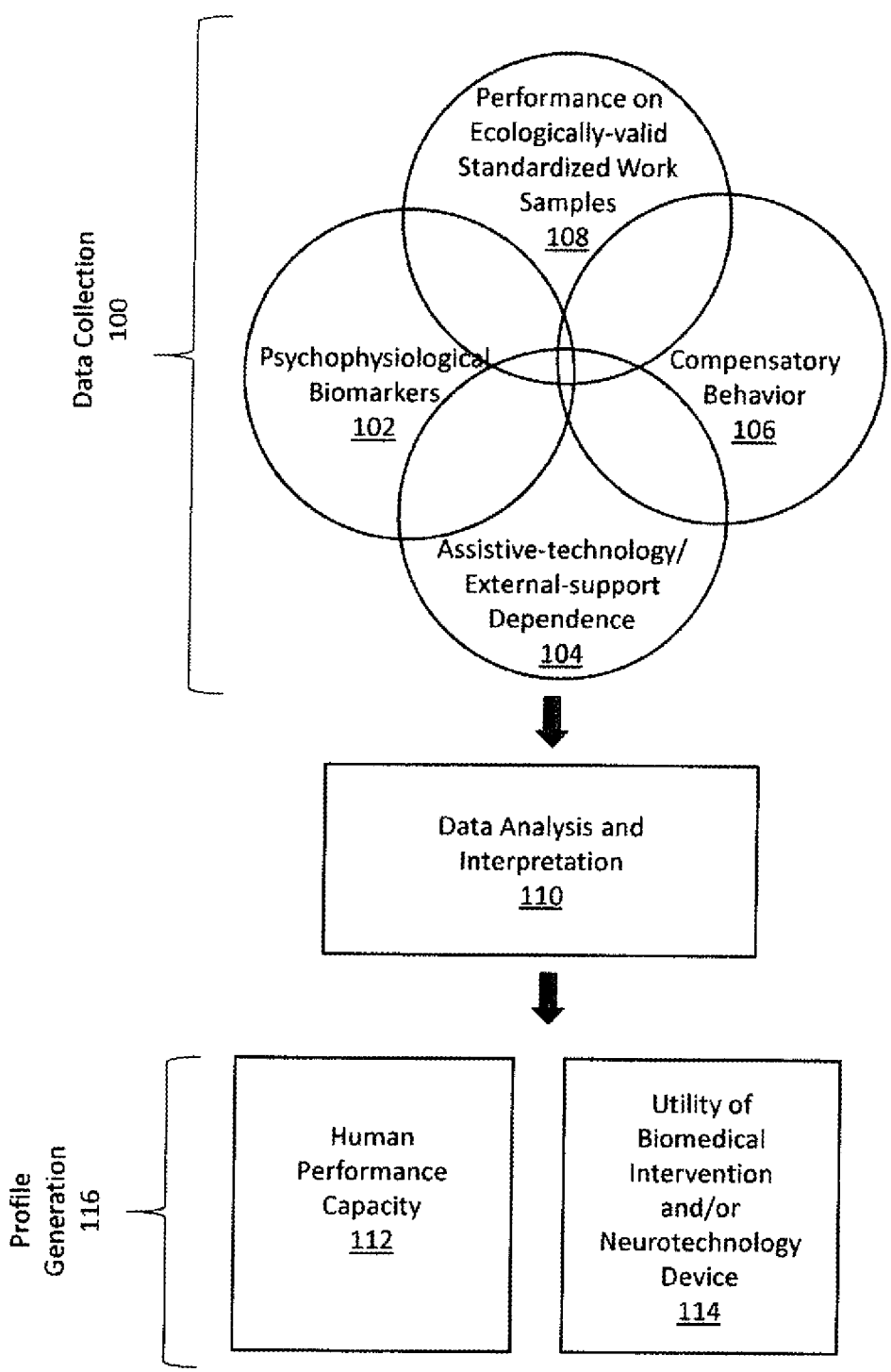
FIG. 1 is a schematic diagram of a system and method for determining human performance capacity and determining the utility of a given biomedical intervention and/or neurotechnology device in one embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

After reading this description, it will become apparent to one skilled in the art how to implement the invention in various embodiments. Implementations that diverge from the embodiments described herein nevertheless reside within the spirit and the scope of the present invention. Furthermore, systems and methods for data generation and collection, data analysis and interpretation, and profile generation described herein can be applied to a myriad of embodiments while remaining within the spirit and the scope of the present invention.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

Referring first to FIG. 1, a schematic diagram of a system and method for determining human performance capacity and determining the utility of a given biomedical intervention and/or neurotechnology device is shown in one embodiment of the present invention. Shown are a data collection step 100, a plurality of collected initial data sets 102, 104, 106, 108, a data analysis and interpretation step 110, a profile generation step 116, a human performance capacity profile 112 and a utility of biomedical intervention and/or neurotechnology device profile 114. The term "neurotechnology device" as used herein may refer to neurotechnology devices and/or biomedical interventions.

In the first data collection step 100, data are generated and collected via the system (in one example, the system of FIG. 2) by using non-invasive and/or invasive monitoring/stimulation/adaptive equipment while a person performs an ecologically-valid standardized work sample. As is known in the art, a work sample is an actual job or task or its simulation used in testing a person's ability to perform it. When the person performs the work sample, the person interacts with at least one work sample object. The work sample object may be a tool, an environment, a written test (wherein the interaction may be via hard copy or via computer), etc. Specific work samples as well as data-collection methodologies are selected according to particular embodiments and applications. In the embodiment shown, the data is organized into four initial data sets: Psychophysiological Biomarkers 102 (e.g. cognitive workload and functioning); Assistive-technology/external-support dependence 104 (e.g. degree and/or frequency of usage); Compensatory Behavior 106 (e.g. degree and frequency of usage); and Performance on Ecologically-valid Standardized Work Samples 108 (e.g. rate/quality and/or outcome scores achieved). Data may be included in more than one initial data set, as shown by the overlapping initial data sets 102, 104, 106, 108 in FIG. 1.

During the data collection step 100, for example, data regarding a person's performance on a work sample is collected via criterion-referenced, norm-referenced, and/or other methods. Data regarding psychophysiological biomarkers associated with cognitive workload and functioning may be collected using non-invasive methods such as electroencephalography (in the case of p300 event related potentials and alpha-wave power changes, for example), subjective reports, or by using invasive methods such as blood-sampling. Such data may be collected and organized as nominal, ordinal, interval, or ratio sets as desired. Data regarding assistive-technology/external-support dependence are collected via observation (in the case of devices of lesser sophistication, such as electronic scratch pads) or via electronically-generated information streams (in the case of devices of greater sophistication, such as adaptively-automated task-management software or neurofeedback devices). As is known in the art, assistive-technology/external-support (also referred to as assistive technology and/or external support) is any item, piece of equipment, software program, or product system that is used to increase, maintain, or improve the functional capabilities of a person. As above, such data regarding assistive-technology/external-support dependence may be collected and organized as nominal, ordinal, interval, or ratio sets as desired. Data regarding the degree and/or frequency of usage of pharmaceutical compounds may be collected and organized as nominal, ordinal, interval, or ratio sets as desired. Data regarding the degree and/or frequency of usage of direct, invasive/non-invasive brain supports are collected based on benchmarks appropriate to the technology being utilized. For example, in the case of the diverse forms of transcranial stimulation, the percentage of motor evoked potential/motor threshold and/or percentage of phosphene threshold employed may be recorded as a measure of stimulation intensity using an interval value. Likewise, the incidence of stimulation events may be recorded as a nominal or as an ordinal value, and the frequency of the stimulus pulse delivery may be recorded as an interval value expressed in Hertz. Stimulus trains (on time) and intertrain intervals (off time) may also be recorded as a measure of stimulus duration using ordinal, interval, or ratio sets. Regarding a person's usage of an external or implanted sensory-intensification or transmission device, cognitive, motor, or sensory neuroprosthetic/implant, other brain-computer interface, or self-initiated support such as compensatory strategies, the degree and/or frequency of usage is collected and organized as nominal, ordinal, interval, or ratio sets as desired. As will be appreciated by one of ordinary skill in the art, as technology advances, data-collection methods may adapt to any emerging forms of usage quantification. All data values are collected simultaneously and in real-time as the person performs an ecologically-valid standardized work sample.

Cognitive workload measures may be collected via physiological monitoring using a myriad of devices and sensors, including but not limited to, U.S. Pat. No. 6,309,342 to Blazeyet, et al., issued Oct. 30, 2001 and incorporated in its entirety herein by reference. Additional examples include, but are not limited to, B-Alert® from Advanced Brain Monitoring, Enobio® and StarStim® from Neuroelectrics. Inventions such as the method identified in U.S. Pat. No. 9,179,847 to Eggenberger, et al., issued Nov. 10, 2015, which provides physiological monitoring for the purpose of identifying matches between a person and a job via correlations between a person's biometric profile and stored biometric profiles, would not be used, as the system and method described herein yield a more comprehensive profile of a person's performance capacity, given that the level of efficiency (performance score vs. cognitive effort vs. usage of external and/or self-initiated supports) as compared to a plurality of subjects is identified using the system and method, but not via the method identified in the '847 patent. Additionally, inventions such as the methods identified in U.S. Pat. No. 6,726,624 issued Apr. 27, 2004, U.S. Pat. No. 8,135,472 issued Mar. 13, 2012, U.S. Patent Application Publication No. 2011/0004412, published Jan. 6, 2011, U.S. Patent Application Publication No. 2014/0279746, published Sep. 18, 2014, U.S. Patent Application Publication No. 2014/0330576, published Nov. 6, 2014, and US Patent Application Publication No. 2015/0018630, published Jan. 15, 2015, which provide physiological monitoring for the purpose of diagnosis and treatment of medical disease, would not be used.

Regarding the hardware and work samples (also referred to as sensors and data collection devices/modules) utilized during the data collection step 100, examples of hardware and work samples utilized include, but are not limited to, SimWork Systems, Valpar Component Work Sample System, Complex Task Performance Assessment, Weekly Calendaring Planning Activity, Executive Function Performance Test, Warship Commander Task, and Charge of Quarters Duty Task.

Examples of hardware and neurotechnology devices utilized for assessment of cognitive workload include, but are not limited to, B-Alert® from Advanced Brain Monitoring, Enobio®, and StarStim® from Neuroelectrics Examples of hardware, neurotechnology devices and biomedical interventions utilized for assistive-technology/external-support include, but are not limited to, StarStim® from Neuroelectrics, proprietary adaptive automation software, proprietary transcranial radiant energy devices (electrical, magnetic, light-emitting, low-level laser, etc.), and pharmaceutical compounds.

As shown in FIG. 1, In accordance with the present embodiment, the data collection step 100 results in the production of the 4 initial data sets: Psychophysiological Biomarkers of Cognitive Workload and Functioning 102, Assistive-technology/External-support Dependence 104, Compensatory Behavior 106, and Performance on Ecologically-valid Standardized Work Samples 108.

During the next data analysis and interpretation step 110, the initial data sets 102, 104, 106, 108 gathered in the data collection step 100 are subsequently organized into eight data sets, five of which result from the transformation of the data gathered in the data collection step 100 into novel data. The eight data sets also include data from external sources, i.e. data not collected during the performance. The database 208 comprises previously collected data of performances of other persons that are used to compare with the collected data during the data analysis and interpretation step 110.

The eight analyzed data sets include Absolute Performance 300, Relative Performance 302, Relative Effort 304, Absolute Efficiency 306, Relative Efficiency 308, Resource Efficiency 310, Behavioral Efficiency 312, and Composite 400, and are described further below in FIGS. 3 and 4.

Analyzed data sets Absolute Efficiency 306, Relative Efficiency 308, Resource Efficiency 310, Behavioral Efficiency 312, and Composite 400 arise from using the system and method in order to reveal indices as well as interrelationships not previously established in the prior art. Absolute Efficiency 306, Relative Efficiency 308. Resource Efficiency 310, Behavioral Efficiency 312, and Composite 400 are produced via a novel methodology of characterizing human performance capacity as comprised of demonstrated ability versus the investment/usage of resources. Analysis of each data set 300, 302, 304, 306, 308, 310, 312, 400 is used to produce a score for that data set 300, 302, 304, 306, 308, 310, 312, 400.

Absolute Efficiency data set 306 considers the cognitive effort exerted in order to achieve a given performance score, without regard to a plurality of subjects. This analysis results in an Absolute Efficiency score 408.

Relative Efficiency data set 308 considers the cognitive effort exerted in order to achieve the same performance score as a person's peers. In Relative Efficiency 308, a person will score higher if he/she exerts less cognitive effort in order to achieve the same performance score as his/her peers, and he/she will score lower if he/she exerts more cognitive effort in order to achieve the same performance score as his/her peers. This analysis results in a Relative Efficiency score 410.

Resource Efficiency data set 310 considers the amount of assistive technology and/or external supports (also referred to as "assistive-technology/external-support) used by a person in order to achieve a given Relative Efficiency 308 score (from the Relative Efficiency data set 308). In Resource Efficiency 310, a person will score higher if he/she uses less assistive-technology/external-supports in order to achieve a given Relative Efficiency score 410, and he/she will score lower if he/she uses more assistive-technology/external-supports in order to achieve a given Relative Efficiency score 410. Resource Efficiency 310 results in a Resource Efficiency score 412. A person's Resource Efficiency score 412 is then compared to a plurality of subjects, such as the person's peers.

The Behavioral Efficiency data set 312 is similar to Resource Efficiency 310, but relates to a person's behavior rather than to the person's usage of assistive-technology/external resources. Behavioral Efficiency 312 considers the amount of compensatory strategies adopted by a person in order to achieve a given Relative Efficiency score 410. In Behavioral Efficiency 312, a person will score higher if he/she uses fewer compensatory strategies in order to achieve a given Relative Efficiency score 410, and he/she will score lower if he/she uses more compensatory strategies in order to achieve a given Relative Efficiency score 410. Behavioral Efficiency 312 results in a Behavioral Efficiency score 414. The person's Behavioral Efficiency score 414 is then compared to a plurality of subjects, such as the person's peers.

Finally, the Composite data set 400 is regarded as novel because the Composite data set 400 arises from the required inclusion of at least two of the previously described novel data sets 300, 302, 304, 306, 308, 310, 312. In one embodiment, the composite score 400 is based on Absolute Efficiency data set 306, Relative Efficiency data set 308, Resource Efficiency data set 310, and Behavioral Efficiency data set 312. It will be understood that other combinations may be used to tailor the result for specific outcomes. Analysis of the Composite data set 400 results in a Composite score 416.

After the data analysis and interpretation step 110, the method proceeds to the profile generation step 116. During the profile generation step 116 the human performance capacity profile 112 is generated using the system and method in order to detail the rate and/or quality of a person's performance of ecologically-valid standardized work samples, the cognitive effort exerted in order to achieve a given performance score, and the level of efficiency (performance score vs. cognitive effort vs. usage of external and/or self-initiated supports) as compared to a plurality of subjects. In other words, the profile includes one or more of an expectation of the person's work rate and an expectation of the person's work quality. The utility of biomedical intervention and/or neurotechnology device profile 114 requires the human performance capacity profile 112 and is generated to determine the efficacy and the effectiveness, as well as the recommendations for use, of a given biomedical intervention and/or neurotechnology device to characterize, to predict, and to influence human performance capacity.

Referring again to FIG. 1, the method of FIG. 1 relates to the assessment of human performance capacity during reciprocal interactions with neurotechnology, as opposed to using neurotechnology to assess a person's condition for the purpose of medical diagnosis or other goal not associated with functional behavior in naturalistic settings.

Although neurocognitive functioning can influence human performance capacity, no identifiable threshold of neurocognitive functioning has been established for making determinations regarding a person's ability or inability to perform goal-directed real-world activities, regardless of whether or not traditional paper-and-pencil neuropsychological tests (indirect measures of neuronal activity) or whether or not neurophysiological measures (direct measures of neuronal activity) are used. In fact, unless a person is found to be grossly and obviously incapacitated, regardless of diagnosis or of impairment rating, existing assessment methodologies are insufficient for characterizing, predicting, or influencing human performance capacity, particularly regarding a person's ability to perform activities requiring higher-level cognition, such as instrumental activities of daily living and work.

Additionally, although existing performance-based assessments of functional behavior, such as the work samples comprising a cognitive functional capacity evaluation, provide a sound determination of a person's ability or inability to perform goal-directed real-world activities, no objective measurement of an individual's biological and/or neurological condition related to motivation, emotional state, fatigue, use of psychoactive substances, cognitive workload/cognitive effort exerted, reliance on compensatory behaviors, or reliance on external-supports/assistive-technology such as software or invasive/non-invasive brain/biomedical supports is provided.

Clinical studies, practice guidelines, and expert opinion indicating that approaches found in the prior art are not designed to and are incapable of assessing cognitive aspects of human performance capacity include: "Reliability, validity, and clinical utility of the Executive Function Performance Test: A measure of executive function in a sample of people with stroke" by Baum et al. (2008); "The return to work after a neuropsychological programme and the prognostic factors for success" by Bjork (2010); "Assessment of executive functions: Review of instruments and identification of critical issues" by Chan et al. (2007); Improving the ecological validity of executive functioning assessment" by Chaytor et al. (2006); "The art of practicing a science that does not yet exist" by Faust (1991); "Predicting vocational functioning from neuropsychological test data" by Guilmette (2005); "A comparison of neuropsychological and situational assessment for predicting employability after closed head injury" by LeBlanc et al. (2000); *Neuropsychological Assessment* by Lezak et al. (2004); *Rehabilitation for Everyday Adaptive Living* by Ponsford et al. (2013); "Limitations of neuropsychological testing predict the cognitive and behavioral functioning of persons with brain injury in real-world settings" by Sbordone (2001); "Recovery versus retest effects in in attention after closed head injury" by Spikman (1999); and "Initial development of a work-related assessment of dysexecutive syndrome: The complex task performance assessment" by Wolf (2008).

Clinical studies, practice guidelines, and expert opinion indicating that approaches found in the prior art are not designed to and are incapable of assessing physical aspects of human performance capacity include: *Occupational Therapy Expert Opinions on Work Capacity: A Grounded Theory* by Allen (2005). *Guide to the evaluation of functional ability* by the American Medical Association (2009); *Guide to the evaluation of permanent impairment* by the American Medical Association (2009); "Enhancing the conceptual clarity of the activity and participation components of the International Classification of Functioning, Disability, and Health" by Badley (2008); "The genesis of handicap: Definition, models of disablement, and the role of external factors" by Badley (1995); "Sitting and standing tolerance in patients with chronic back pain: Comparison between physician prediction and covert observation" by Brokaw et al. (2004); "Comparing self-report, clinical examination and functional testing in the assessment of work-related limitations in patients with chronic low back pain" by Brouwer (2005); "Impairment ratings for back claims are poor predictors of wage loss" by Butler et al. (2000). "Does disability correlate with impairment after hand injury?" by Farzad et al. (2015); "Chronic low back pain: the relationship between patient satisfaction and pain, impairment, and disability outcomes" by Hazard et al. (1994): "Functional restoration with behavioral support: a one-year prospective study of patients with chronic low-back pain" by Hazard et al. (1989); "Conceptual issues in the measurement of work disability" by Jette et al. (2000); "Isokinetic trunk strength and lifting strength measures: differences and similarities between low-back-injured and noninjured workers" by Mandell et al. (1993); "The functional capacity evaluation" by Matheson (2003); "Improving the Validity of the Impairment Evaluation Process: A Proposed Theoretical Framework" by Matheson et al. (2000); "Determinants of vocational disability in patients with low back pain" by Milhous et al. (1989): "Assessment of the progress of the backpain patient" by Million et al. (1982); "Impairment, disability, and handicap" by Mooney (1987); *Survey Measurement of Work Disability: Summary of a Workshop*, chapter entitled "Front Matter" by National Research Council (2000); "Trunk strength testing with iso-machines. Part I: Review of a decade of scientific evidence" by Newton et al (1993); "Comparing severity of impairment for different permanent upper extremity musculoskeletal injuries" by Reville et al (2002); "Comparative roentgenographic study of the asymptomatic and symptomatic lumbar spine" by Torgerson et al. (1978); "Impairment and disability after severe hand injuries with multiple phalangeal fractures" by Van Oosterom et al (2007); "Objective clinical evaluation of physical impairment in chronic low back pain" by Waddell et al. (1992); "Assessment of severity in low-back disorders" by Waddell et al (1984); and "Effect of Functional Capacity Evaluation information on the judgment of physicians about physical work ability in the context of disability claims" by Wind et al. (2009).

The present embodiments provide a novel system and method of transforming raw data representative of certain physical parameters, such as abilities, actions, and/or phenomena, into data representative of non-obvious and novel physical parameters. The raw data collected in the data collection step 100 comprises raw biological, assistive-technology, behavioral, and performance-based initial data sets 102, 104, 106, 108. The conclusion data included in the subsequently generated profiles 112, 114 include quantitative indices of ability to perform real-world activities such as basic and instrumental activities of daily living and work, also known as human performance capacity, and/or the efficacy and the effectiveness, as well as the recommendations for use, of a given biomedical intervention and/or neurotechnology device to characterize, to predict, and to influence human performance capacity.

The system and method of FIG. 1 is used to characterize, predict, and influence a person's performance capacity based on the analysis and interpretation of 1) psychophysiological biomarkers of cognitive workload and functioning, 2) degree and/or frequency of usage of assistive-technology/external-supports, 3) degree and/or frequency of usage of activity modifications or compensatory behavior, and 4) the rate and/or quality of goal-directed real-world activity performance. The system and method are based on the simultaneous recording and interpretation of 1) indicators of a person's cognitive workload and functioning, such as p300 and other event-related potentials; cerebral blood flow via functional transcranial Doppler ultrasound; metabolic and/or anatomic data elucidated via positron emission tomography and functional magnetic resonance imaging; electroencephalography and magnetoencephalography; metabolites associated with cognitive activity; pupillary dilation and other eye movements; other somatic data such as heart rate, blood pressure, rate of respiration, body temperature, and/or galvanic skin response; subjective reports, including impressions of effort exerted and perceived stressfulness of the task; and other biological and/or behavioral measures, 2a) indicators of mitigation of task demands, such as postponement/reallocation, modification, or interpretation/elimination of challenging activity components by an intervening party, an artificially-intelligent personal assistant, and/or by an adaptively-automated system, 2b) indicators of usage of technologies which augment cognition and/or information, motor, or sensory processing ability, including pharmaceutical compounds, neurofeedback devices which train users to adopt a specific cognitive state, external as well as implanted sensory-intensification or transmission devices such as night-vision goggles and cochlear implants, and invasive/non-invasive brain supports, such as transcranial direct-current stimulation, transcranial magnetic stimulation, transcranial light-emitting diodes, transcranial ultrasound, cognitive, motor, or sensory neuroprostheses/implants, other radiant-energy technologies, and/or brain-computer interfaces, 3) indicators of usage of self-initiated supports, such as a person's adoption of compensatory strategies, and 4) performance scores on ecologically-valid standardized work samples.

The system and method render the human performance capacity profile 112 detailing the rate and/or quality of the person's performance of ecologically-valid standardized work samples, the cognitive effort exerted in order to achieve a given performance score, and the level of efficiency (performance score vs. cognitive effort vs. usage of external and/or self-initiated supports) as compared to a plurality of subjects. The person's human performance capacity profile 112 is used to assess performance capacity, or the ability to perform real-world activities such as basic and instrumental activities of daily living as well as work. The system and method are used to make home-discharge and vocational-placement recommendations for person's following an injury and/or rehabilitation, to conduct veracity assessments in the litigation/forensic setting, and to establish an uninjured/typical person's fitness-for-duty for settings in which the system and method are both relevant and can be ethically and legally utilized (e.g.: military/government applications, civilian jobs in which the commission of errors would result in a critical public-safety risk). Additionally, given that the system and method monitor the impact of assistive-technology/external-supports on a person's ability to perform real-world activities, the system and method are also used to determine the efficacy and the effectiveness, as well as the recommendations for use, of a given biomedical intervention and/or neurotechnology device to characterize, to predict, and to influence human performance capacity, including for individual persons as well as for populations of persons comprised of shared and/or divergent characteristics.

Given that the system and method monitor the impact of assistive-technology/external-supports on a person's ability to perform real-world activities, such as the impact of adaptively automated systems (U.S. Pat. No. 4,683,891 to Cornellier et al., issued Aug. 4, 1987, U.S. Pat. No. 5,724,987 to Gevins et al., issued Mar. 10, 1998, U.S. Pat. No. 9,251,716 to Drane et al., issued Feb. 2, 2016, and U.S. Patent Application Publication No. 2014/0335480, published Nov. 13, 2014, all of which are incorporated herein by reference), biofeedback devices (U.S. Patent Application Publication No. 2009/0069707, published Mar. 12, 2009, incorporated in its entirety herein by reference), combined adaptively automated systems and biofeedback devices (U.S. Patent Application Publication No. 2016/0007915, published Jan. 14, 2016, incorporated in its entirety herein by reference), and other devices and substances which alter or augment cognition (e.g.: pharmaceutical compounds, neurofeedback devices which train users to adopt a specific cognitive state, invasive/non-invasive brain supports, such as transcranial direct-current stimulation, transcranial magnetic stimulation, transcranial light-emitting diodes, transcranial ultrasound, cognitive prostheses, other radiant-energy technologies, and/or brain-computer interfaces), the profile generated by the system and method is also used to determine the efficacy and the effectiveness, as well as the recommendations for use, of a given biomedical intervention and/or neurotechnology product to characterize, to predict, and to influence human performance capacity. Such a feature enables the user of the system and method to directly compare and rank biomedical interventions and/or neurotechnology products against each other by degree of utility, as well as to fine tune or otherwise alter a product based on the information gleaned from usage of the system and method. Furthermore, for purposes of modeling and simulation, once a pattern of interaction between the data sets is identified, digital emulations of a single person or of a given population may be constructed, and single or multiple variables may be manipulated in order to determine the impact that changing a select variable or a set of variables will have on other variables, thus enabling an infinite variety of computer-mediated investigations without the direct use of human subjects.

The present embodiments typically require employing machines and/or computers (such as electroencephalography equipment, radiant-energy equipment, etc.), in addition to other specialized sensors and apparatus, in order to generate and/or collect the data essential for the embodiment's use.

Additionally, the present embodiments typically require employing machines and/or computers in order to enable rapid processing and manipulation of collections of large data sets.

The data collection requires the usage of an unnatural device and apparatus (radiant-energy equipment, cognitive prosthetic, brain-computer interface, etc.) in order to generate data related to performance that would otherwise not exist absent the usage of the present embodiments.

Additionally, the profiles can be used as grounds for action, such as whether or not a person moves forward in a rehabilitation and/or selection process, or whether or not a neurotechnology device moves forward in a research and/or marketing pipeline or requires fine tuning or should be otherwise modified.

Although the present embodiments pertain to the simultaneous and real-time generation, recording, and interpretation of data, in some embodiments select aspects of the system and method can be utilized following the person's interaction with assistive-technology/external-supports (i.e.: biomedical interventions and/or neurotechnology devices) in order to assess any residual effects that using assistive-technology/external-supports will have on the variables under investigation, such as the person's delayed and/or long-term performance capacity as well as the post-interaction efficacy and the effectiveness, as well as the recommendations for use, of a given biomedical intervention and/or neurotechnology device to characterize, to predict, and to influence human performance capacity.

In other embodiments the system and method may be used in order to assess the performance capacity of non-human subjects, including digital emulations of subjects composed of user-assigned traits, as well as hybridized human-computer embodiments, such as avatars operating in virtual-reality environments as well as reality-based telepresence robots or remotely-controlled human-surrogate machines operated via brain/body-computer interface.

In one example, the method and system of FIG. 1 are used to determine a person's ability to return to work as an Electronic Equipment Assembler following rehabilitation for a cerebral vascular accident. The example includes instructing the person to perform a criterion-referenced work sample that has been standardized using data obtained via methods-time measurement analysis. During performance of the work sample, psychophysiological data are collected from the person, including but not limited to data identifying the cognitive effort exerted in order to perform the activity. Additionally, the degree and/or frequency of postponement/reallocation of the delivery of parts via an adaptively automated production system as well as the degree and/or frequency of compensatory strategies adopted by the person (such as the elimination and/or modification of challenging activities) are documented. Furthermore, the degree and/or frequency of usage of direct, invasive/non-invasive brain supports such as a cognitive prosthesis are documented. After the data are analyzed and interpreted, rehabilitation as well as vocational-placement recommendations are provided. Additionally, the system and method are used to determine the efficacy and the effectiveness, as well as the recommendations for use, of the employed biomedical interventions and/or neurotechnology devices (adaptively automated production system, cognitive prosthesis) to characterize, to predict, and to influence human performance capacity.

In another example, the method and system of FIG. 1 are used to assess the veracity of a person's claim of an inability to work as a Clerical Assistant following a traumatic brain injury The example includes instructing the person to perform a criterion- and/or norm-referenced work sample. During performance of the work sample, psychophysiological data are collected from the person, including but not limited to data identifying the cognitive effort exerted in order to perform the activity. Additionally, the degree and/or frequency of compensatory strategies adopted by the person (such as the elimination and/or modification of challenging activities) are documented, in addition to the person's degree and/or frequency of usage of adaptively automated assistive technology. Furthermore, the degree and/or frequency of usage of direct, invasive/non-invasive brain supports such as transcranial magnetic stimulation are documented. After the data are analyzed and interpreted, an assessment of claim veracity is provided. Additionally, the system and method are used to determine the efficacy and the effectiveness, as well as the recommendations for use, of the employed biomedical interventions and/or neurotechnology devices (adaptively automated assistive technology, transcranial magnetic stimulation) to characterize, to predict, and to influence human performance capacity.

In yet another example, the method and system of FIG. 1 is used to establish an uninjured/typical person's fitness for duty as an Air Traffic Controller. The example includes instructing the person to perform a criterion- and/or norm-referenced work sample. During performance of the work sample, psychophysiological data are collected from the person, including but not limited to data identifying the cognitive effort exerted in order to perform the activity. Additionally, the degree and/or frequency of postponement/reallocation, modification, or elimination of challenging activity components by an adaptively automated computer workflow-management system are documented. Furthermore, the degree and/or frequency of usage of direct, invasive/non-invasive brain supports such as transcranial direct-current stimulation are documented. After the data are analyzed and interpreted, fitness or non-fitness for duty is established. Additionally, the system and method are used to determine the efficacy and the effectiveness, as well as the recommendations for use, of the employed biomedical interventions and or neurotechnology devices (adaptively automated computer workflow-management system, transcranial direct-current stimulation) to characterize, to predict, and to influence human performance capacity.

In yet another example, the method and system of FIG. 1 are used to determine which biomedical intervention and/or neurotechnology device among an array of biomedical interventions and/or neurotechnology devices most improves or otherwise impacts a person's ability to perform a cognitively-demanding functional task, also known as the device's utility. The example includes instructing the person to perform an ecologically-valid criterion- and/or norm-referenced work sample (such as Air Traffic Controller) while using various biomedical interventions and/or neurotechnology devices, followed by comparing the performance scores obtained in the context of the cognitive effort exerted, the degree and/or frequency of usage of assistive technology and/or external supports, and the degree and/or frequency of activity modifications or compensatory behavior while using each different biomedical intervention and/or neurotechnology device. Changes in the various data sets can be attributed to the introduction of a given biomedical intervention and/or neurotechnology device, thus enabling the user of the system and method to determine the efficacy and effectiveness, as well as the recommendations for use, of a given biomedical intervention and/or neurotechnology device to characterize, to predict, and to influence human performance capacity. Such a process may be employed in order to determine which biomedical intervention and/or neurotechnology device most improves or otherwise impacts a single person's performance capacity. Additionally, such a process may be used in order to determine which biomedical intervention and/or neurotechnology device most improves or otherwise impacts a given population's (worker type, disease/patient type, etc.) performance capacity. Furthermore, as such a process assesses the efficacy and the effectiveness, as well as the recommendations for use, of a given biomedical intervention and/or neurotechnology device based on the impact that the biomedical intervention or neurotechnology device usage has on human performance capacity, the process described herein can be used to directly compare and rank devices (and/or interventions) against each other by degree of utility, as well as to fine tune, later otherwise adjust a biomedical intervention or neurotechnology device based on the information gleaned from usage of the system and method.

Additionally, as with all of the embodiments described herein, for purposes of modeling and simulation, once a pattern of interaction between the data sets is identified, digital emulations of a single person or of a given population may be constructed, and single or multiple variables may be manipulated in order to determine the impact that changing a select variable or a set of variables will have on other variables, thus enabling an infinite variety of computer-mediated investigations without the direct use of human subjects. Finally, interrelationships between independent and/or dependent variables revealed through usage of the system and method will also inform general as well as specialized research regarding physiological/neurophysiological functioning, human performance capacity, and neurotechnology.

Figure 2:
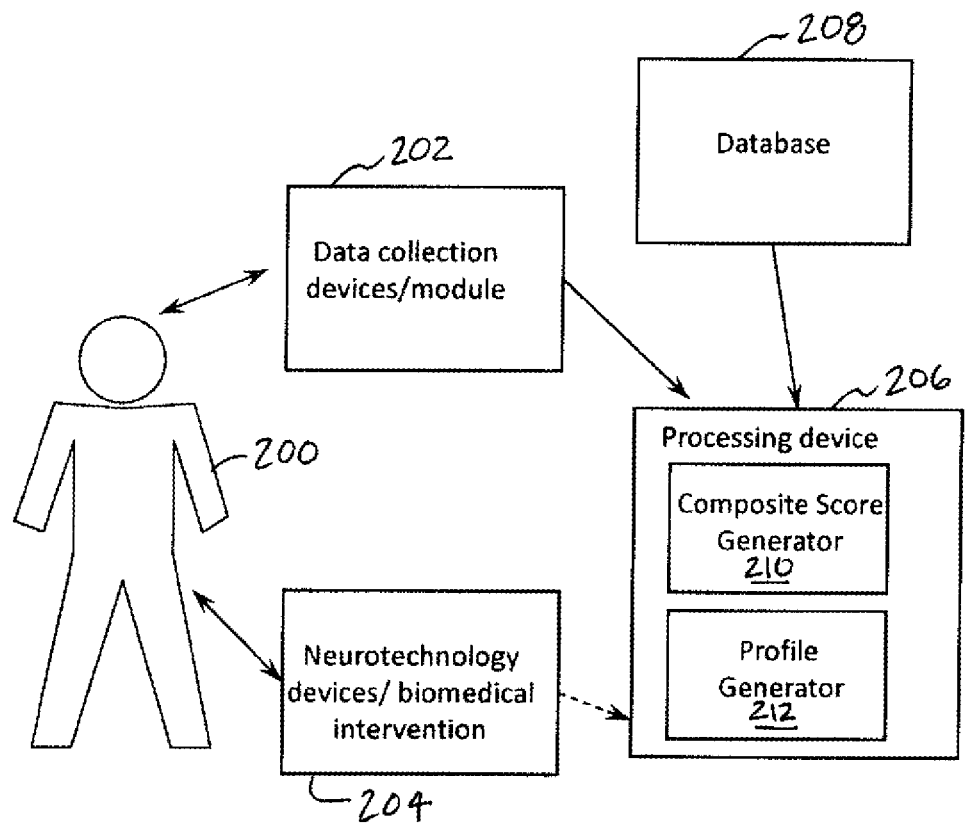
FIG. 2 is an exemplary system for carrying out the method of FIG. 1.

Referring next to FIG. 2, an exemplary system for carrying out the method of FIG. 1 is shown. Shown are a person 200, at least one data collection device/module 202, at least one neurotechnology device/biomedical intervention 204, a processing device 206, and database 208.

During the data collection step 100, the person 200 interacts with the at least one data collection device/module 202 during the work sample and/or other performance task. Data collected during the performance is sent to the processing device 206. The processing device 206 is a computing device configured to receive, store and process the data in accordance with the systems and methods described herein.

During the data collection step 100, the person 200 also interacts with the neurotechnology device/biomedical intervention 204 during the work sample and/or or other performance task. In some embodiments data is collected by the neurotechnology device/biomedical intervention 204 and sent to the processing device 206.

The processing device 206 also receives the database 208 as previously described, which is used by the processing device 206 during the data analysis and interpretation step 110 (along with the data collected from the person 200) and the profile generation step 116.

Referring next to FIG. 3, a table detailing the analysis of the analyzed data sets of the data analysis and interpretation step 110 (with the exception of the Composite data set 400) is shown. Shown are the data sets 300, 302, 304, 306, 308, 310 and 312. For each data set 300, 302, 304, 306, 308, 310, 312, construct entities compared and mathematical description for resulting score are shown.

For the Absolute Performance data set 300, the construct (i.e. the theoretical and/or practical concept being assessed) is performance. The entities compared are the person vs. the work sample. The mathematical analysis of the data is a percentage based on Methods-Time Measurement (MTM) performance standard (i.e., <70=below competitive, 70-80=entry level, 80-100=competitive, and >100=above competitive). The score is criterion-referenced. The Absolute Performance score 402 is based on the performance rate/quality as compared to a given threshold and/or industry standard. Questions answered by the Absolute Performance score 402 include, "How does this person's performance compare to the standard for the industry and/or setting?"

For the Relative Performance data set 302, the construct is also performance. The entities compared are person vs. person. The mathematical analysis of the data uses standard psychometrics (i.e.: raw score, standard score, scaled score, percentile rank, etc.), and is norm-referenced. The Relative Performance score 404 is based on the performance rate/quality of the person as compared to age/sex/etc.-matched peers. Questions answered by the Relative Performance score 404 include, "How does this person's performance compare to his/her age/sex/etc.-matched peers?"

For the Relative Effort data set 304, the construct is effort. The entities compared are person vs. person. The mathematical analysis of the data is standard psychometrics, norm-referenced. The Relative Effort score 406 is based on the cognitive effort exerted (e.g.: p300, EEG alpha-wave power, etc.) by the person, as compared to age/sex/etc.-matched peers. Questions answered by the Relative Effort score 406 include, "How much cognitive effort is this person exerting as compared to his/her age/sex/etc.-matched peers?"

For the Absolute Efficiency data set 306, the constructs are performance and effort. The entities compared are person vs. self. The mathematical analysis is a ratio between the raw performance score from the person's work sample and the raw effort score. The format of the raw effort score is dependent on the type of measurement; for example, if the raw effort score is obtained from an EEG, the raw effort score may be expressed in frequency or amplitude change. If the raw effort score is based on subjective reports, the raw effort scale may be based on a simple numerical scale. Questions answered by the Absolute Efficiency score 408 include, "How efficient is this person's performance, regardless of whether or not he/she meets the standard for the industry and/or setting, and regardless of how his/her performance compares to his/her age/sex/etc.-matched peers?"

For the Relative Efficiency data set 308, the constructs are performance and effort. The entities compared are person vs. person. The mathematical analysis uses standard psychometrics, norm-referenced. The Relative Efficiency score 410 is based on the cognitive effort exerted as compared to age/sex/etc.-matched peers with the same performance score. Questions answered by the Relative Efficiency score 410 include, "How much cognitive effort must this person exert in order to achieve the same performance score as his/her age/sex/etc.-matched peers?"

For the Resource Efficiency data set 310, the constructs are performance, effort, augmentation and mitigation. The entity is person vs. self. The mathematical analysis involves nominal, ordinal, interval, and ratio analysis, and/or standard psychometrics. The Resource Efficiency score 412 is based on the above Relative Efficiency score 410 as compared to the amount of assistive technology and/or external support required (e.g.: augmentation in the form of tDCS or TMS, pharmaceutical compound usage, etc.; mitigation in the form of activity simplification and/or modification via an intervening party and/or an adaptively automated system; adaptive equipment usage; etc.) Questions answered by the Resource Efficiency data score 412 include, "What type or amount of external supportive resources does this person require in order to achieve a given Relative Efficiency?"

The Resource Efficiency data set 310 can also be used in a person vs. person comparison, with the mathematical analysis involving standard psychometrics, norm-referenced. A person-to-person Resource Efficiency score is based on the Resource Efficiency score 412 as compared to age/sex/etc.-matched peers. Questions answered by the person-to-person Resource Efficiency score include, "How does this person's Resource Efficiency score compare to his/her age/sex/etc.-matched peers?"

For the Behavioral Efficiency data set 312, the constructs are performance, effort and compensation. The entity is person vs. self, mathematical analysis involves nominal, ordinal, interval, and ratio analysis, and/or standard psychometrics. The Behavioral Efficiency score 414 is based on the above Relative Efficiency score 410 as compared to the amount of compensatory strategies adopted (e.g.: person-initiated activity simplification and/or modification). Questions answered by the Behavioral Efficiency score 414 include. "What type or amount of self-initiated supportive behaviors does this person require in order to achieve a given Relative Efficiency?"

The Behavioral Efficiency data set 312 can also be used in a person vs. person comparison, with the mathematical analysis involving standard psychometrics, norm-referenced. A person-to-person Behavioral Efficiency score is based on the Behavioral Efficiency score 414 as compared to age/sex/etc.-matched peers. Questions answered by the person-to-person Behavioral Efficiency score include, "How does this person's Behavioral Efficiency score compare to his/her age/sex/etc.-matched peers?"

Figure 4:
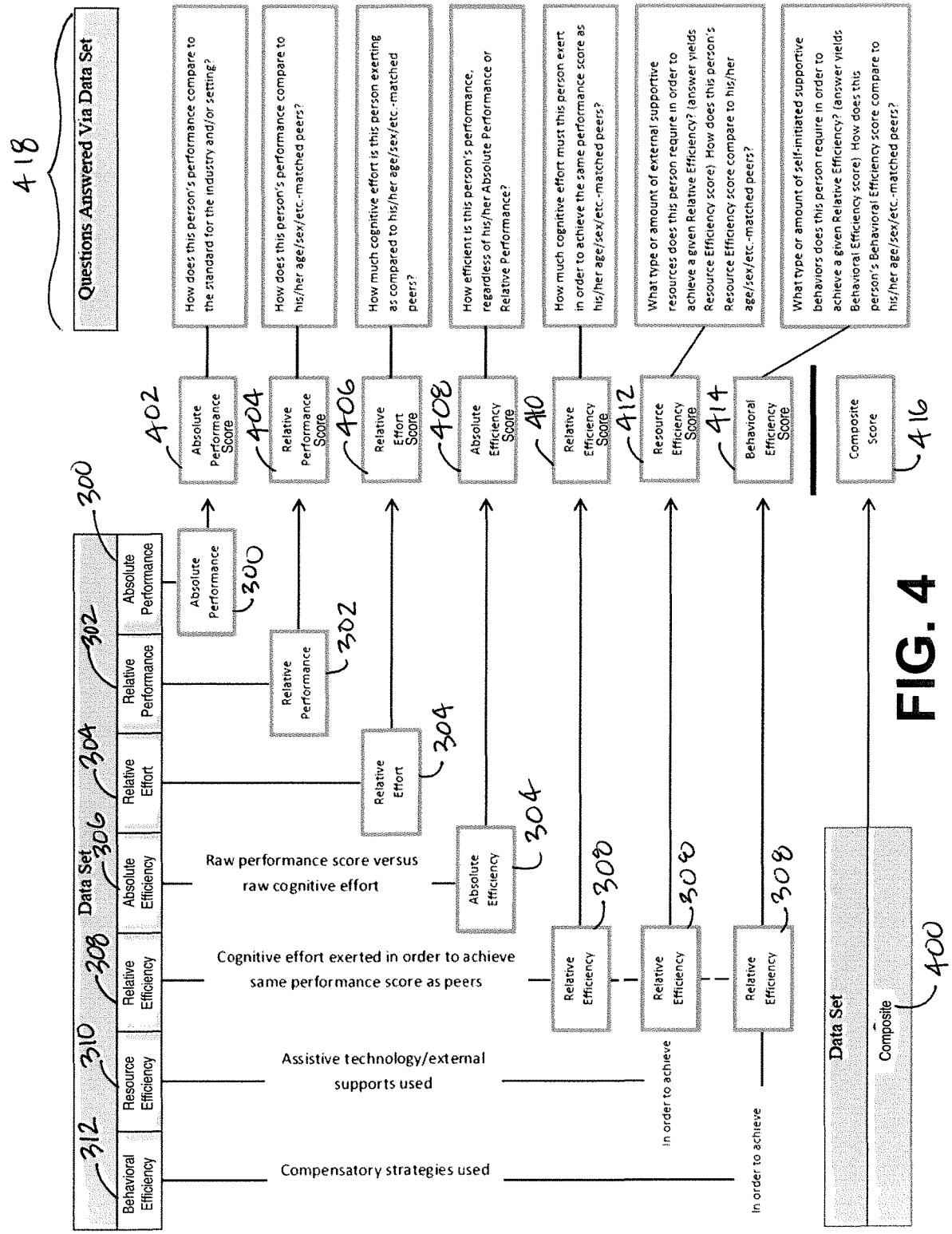
FIG. 4 is a schematic diagram of the analyzed data sets and associated scores.

Referring next to FIG. 4, a schematic diagram of the analyzed data sets and scores is shown. Shown are the Absolute Performance data set 300, the Relative Performance data set 302, the Relative Effort data set 304, the Absolute Efficiency data set 306, the Relative Efficiency data set 308, the Resource Efficiency data set 310, the Behavioral Efficiency data set 312, the Composite data set 400, the Absolute Performance score 402, the Relative Performance score 404, the Relative Effort score 406, the Absolute Efficiency score 408, the Relative Efficiency score 410, the Resource Efficiency score 412, the Behavioral Efficiency score 414, the Composite score 416, and a plurality of questions answered via data set 418.

The information shown in the table of FIG. 3 is shown in graphical form in FIG. 4. The Absolute Performance 300, Relative Performance 302, Relative Effort 304, Absolute Efficiency 306, and Relative Efficiency 308 data sets are analyzed (as described in FIG. 2) to produce the Absolute Performance score 402, the Relative Performance score 404, the Relative Effort score 406, the Absolute Efficiency score 408, and the Relative Efficiency score 410. The Resource Efficiency data set 310 is analyzed in conjunction with the Relative Efficiency score 410 to produce the Resource Efficiency score 412. The Behavioral Efficiency data set 312 is analyzed in conjunction with the Relative Efficiency score 410 to produce the Behavioral Efficiency score 414. At least two of the scores 402, 404, 406, 408, 410, 412, 414 are combined to produce the composite score 416. The scores are typically produced using one or more standard psychometric norming systems known in the art, such as standard score, scaled score, z-score, percentiles, etc., in addition to other methods for specific scores described herein.

As previously described, each score answers at least one question. As illustrated in FIG. 4, exemplary questions answered are shown in the questions answered via data set 418. As shown in FIG. 4, for the Absolute Performance score 402, questions answered via data set 418 include. "How does this person's performance compare to the standard for the industry and/or setting?"

For the Relative Performance score 404, questions answered via data set 418 include, "How does this person's performance compare to his/her age/sex/etc.-matched peers?"

For the Relative Effort score 406, questions answered via data set 418 include, "How much cognitive effort is this person exerting as compared to his/her age/sex/etc.-matched peers?"

For the Absolute Efficiency score 408, questions answered via data set 418 include, "How efficient is this person's performance, regardless of his/her Absolute Performance of Relative Performance?

For the Relative Efficiency score 410, questions answered via data set 418 include, "How much cognitive effort must this person exert in order to achieve the same performance score as his/her age/sex/etc.-matched peers?"

For the Resource Efficiency data score 412, questions answered via data set 418 include, "What type or amount of external supportive resources does this person require in order to achieve a given Relative Efficiency?", as the Resource Efficiency score 412 is defined as the type or amount of external supportive resources required in order to achieve a given Relative Efficiency score 410. For the person-to-person Resource Efficiency score, questions answered via data set 418 by the person-to-person Resource Efficiency score include, "How does this person's Resource Efficiency score compare to his/her age/sex/etc.-matched peers?"

For the Behavioral Efficiency score 414, questions answered via data set 418 include, "What type or amount of self-initiated supportive behaviors does this person require in order to achieve a given Relative Efficiency?", as the Behavioral Efficiency score 414 is defined as the type or amount of self-initiated supportive behaviors required in order to achieve a given Relative Efficiency score 410. For the person-to-person Behavioral Efficiency score, questions answered by include. "How does this person's Behavioral Efficiency score compare to his/her age/sex/etc.-matched peers?"

Figure 5:
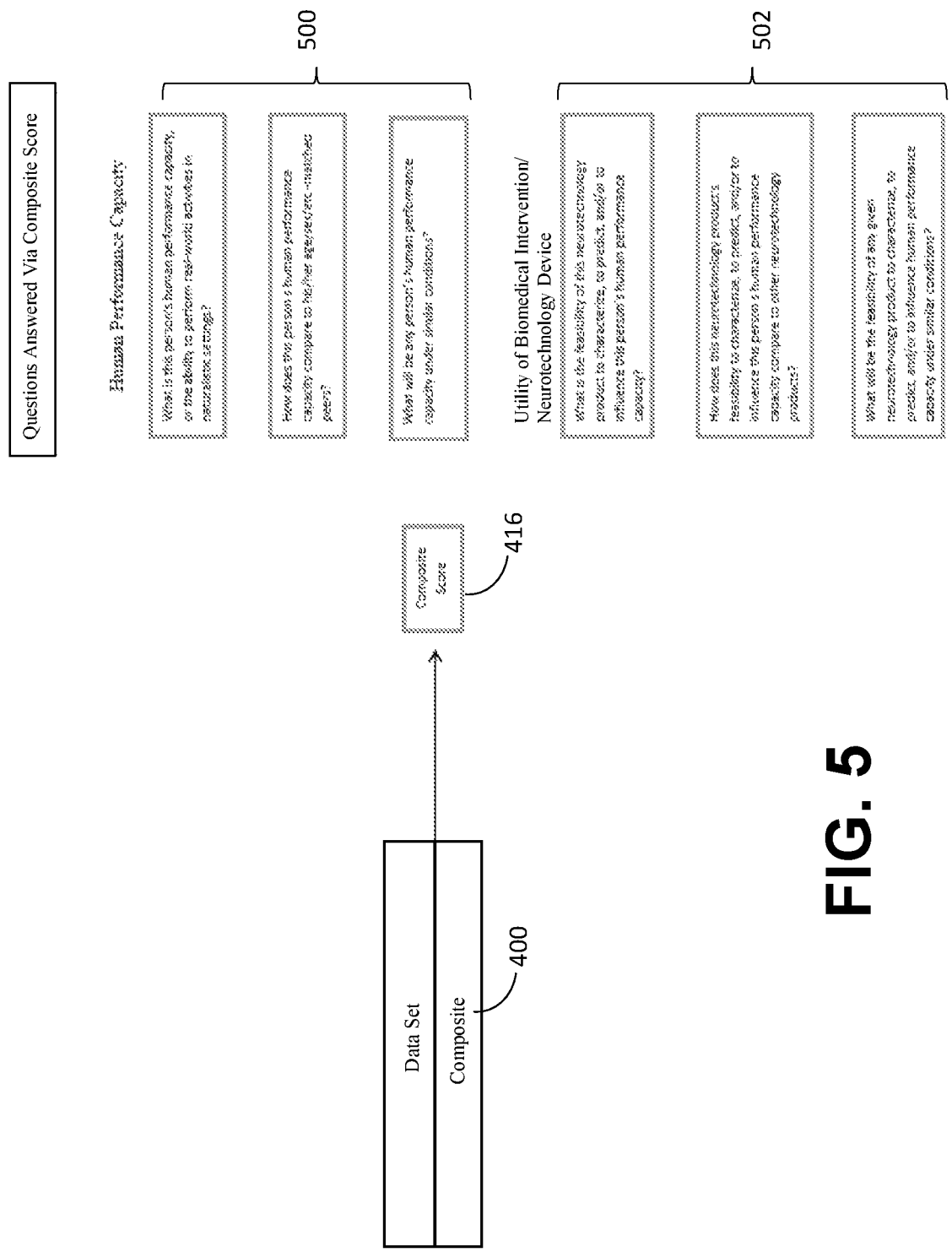
FIG. 5 is a schematic diagram of the analyzed composite data sets and score.

Referring next to FIG. 5, a schematic diagram of the analyzed composite data sets and score is shown. Shown are the composite data set 400, the composite score 416, a plurality of human performance capacity questions answered via composite score 500, and a plurality of utility of neurotechnology device/biomedical intervention questions answered via composite score 502.

The composite score 416 can answer questions regarding human performance capacity and/or utility of the neurotechnology device (product)/biomedical intervention 204. Human performance capacity questions answered via composite score 500 include, "What is this person's human performance capacity, or the ability to perform real-world activities in naturalistic settings," "How does this person's human performance capacity compare to his/her age/sex/etc.-matched peers," and "What will be any person's human performance capacity under similar conditions?"

Utility of neurotechnology device/biomedical intervention questions answered via composite score 502 include, "What is the feasibility of this neurotechnology device to characterize, to predict, and/or to influence this person's human performance capacity," "How does this neurotechnology device's feasibility to characterize, predict, and/or to influence this person's human performance capacity compare to other neurotechnology devices," and "What will be the feasibility of any given neurotechnology device to characterize, to predict, and/or to influence human performance capacity under similar conditions?"

Referring next to FIG. 6, an exemplary subject A profile 600 and an exemplary subject B profile 602 for a first analysis comparing two subjects is shown.

As shown in FIG. 4, both subject "A" and subject "B" are utilizing the same neurotechnology device "X". The result using the previously described method and system result in the subject A human performance capacity profile 600 and the subject B human performance capacity profile 602, as shown in FIGS. 5 and 6.

The Absolute Performance score 402 for subject A is 77 and for subject B is 75. As in determining the Absolute Performance score 402, all subjects' performance rate and quality have been compared to a threshold performance standard, the Absolute Performance score 402 is a criterion-referenced score. In example of FIGS. 5 and 6, Absolute Performance scores 402 and Absolute Efficiency scores 408 are not included in the total composite scores 416, but are reported as distinct values, illustrating the invention's inherent capacity to accommodate the user's particular form of tailored interface.

The Relative Performance score 404 for subject A is 113 (81$^{st}$ percentile), and for subject B is 91 (27$^{th}$ percentile).

The Relative Effort score 406 for subject A is 96 (40$^{th}$ percentile), and for subject B is 103 (58$^{th}$ percentile). Prior to the psychometric analysis, raw data values are inverted in order to ensure that higher standard score values correspond with lower effort exertion.

The Absolute Efficiency score 408 for subject A is 1.25 and for subject B is 1.75. For the given Air Traffic Controller work sample, raw performance scores are divided by raw effort scores. As with Absolute Performance scores 402, in this example the Absolute Efficiency scores 408 are not included in the Composite score 416.

The Relative Efficiency score 410 for subject A is 80 (9$^{th}$ percentile), and for subject B is 117 (87$^{th}$ percentile). As with the Relative Effort score 406, prior to the psychometric analysis, raw data values are inverted in order to ensure that higher standard score values correspond with lower effort exertion.

The Resource Efficiency score 412 for subject A is 76 (5$^{th}$ percentile), and for subject B is 130 (98$^{th}$ percentile). As with the Relative Effort score 406, prior to the psychometric analysis, raw data values are inverted in order to ensure that higher standard score values correspond with lower effort exertion.

The Behavioral Efficiency score 414 for subject A is 88 (21$^{st}$ percentile), and for subject B is 112 (79$^{th}$ percentile). As with the Relative Effort score 406, prior to the psychometric analysis, raw data values are inverted in order to ensure that higher standard score values correspond with lower effort exertion.

Referring next to FIG. 7, an exemplary subject A composite profile 700 and an exemplary subject B composite profile 702 for the first analysis comparing two subjects is shown.

In the composite profiles 700, 702 of the first example, the Absolute Performance score 402 and Absolute Efficiency scores 408 of FIG. 5 are repeated. Also included is the Composite Score 416: for subject A, 86 (18$^{th}$ percentile) and for subject B, 115 (84$^{th}$ percentile).

Referring again to FIGS. 6 and 7, by employing the present invention's novel system and method, in which two different subjects perform the same functional activities while using the same biomedical interventions and/or neurotechnology devices, the performance capacities (fitness for duty as an Air Traffic Controller) of subject A and subject B are assessed and compared using objective representations. Additionally, the complex and multidimensional constructs of human performance capacity are simplified into data sets that facilitate a direct comparison between subject A and subject B.

For example, the present embodiment enables the user to identify subject A's low Relative Efficiency score 410 as an indicator of elevated cognitive effort exertion as compared to subject A's age/sex/etc.-matched peers with the same performance score. Such a result may indicate concerns regarding subject A's overall endurance, despite subject A's favorable Relative Performance score 404. Additionally, the present embodiment enables the system in accordance with the method to identify subject A's low Resource Efficiency score 412 as an indicator of elevated utilization of assistive-technology/external-supports. Furthermore, the present embodiment highlights for the user subject A's low Relative Efficiency score 410, indicating elevated cognitive-effort exertion, despite the concomitant elevated usage of supportive resources. Given subject A's profile, if working as an Air Traffic Controller, subject A is identified as best-suited for settings requiring less endurance, for settings offering consistent access to assistive-technology/external-supports, and for settings that afford consistent opportunities to employ compensatory strategies, given the marginal Behavioral Efficiency score 414. Finally, given that subject A does not exhibit an Absolute Performance score 402 greater than 100, overpacing is not suspected as an explanation for the worsened profile.

But subject B presents with a contrasting profile. Despite exhibiting both Absolute Performance score 402 and Relative Performance score 404 lower than subject A's, subject B's higher Absolute Efficiency score 408, Relative Efficiency Score 410, Resource Efficiency score 412, and Behavioral Efficiency score 414 indicate that, if working as an Air Traffic Controller, subject B may be identified as best-suited for settings requiring greater endurance, for settings offering minimal to no access to assistive-technology/external-supports, and for settings that afford minimal to no opportunities to employ compensatory strategies. Subject B's robust Total Composite Score 416 reflects this overall resilience as an Air Traffic Controller. Furthermore, as indicated by subject B's high Relative Efficiency score 410, subject B presents with an elevated cognitive reserve capacity.

Finally, the above example consists of an analysis of only two subjects as compared to a plurality of subjects. In order to maximize the present embodiment's utility, as well as the utility of the example detailed below in FIGS. 8 and 9, the novel system and method are intended to be employed with a large number of subjects and with machine and/or computer support in order to increase data calculation speed as well as flexibility of the invention's use, including utilization of any extemporaneous data filtering according to user preferences, such as if a user prefers to identify and to re-rank a specific subset of subjects above or below a selected cutoff performance threshold. Such rapid processing and manipulation of large data sets would be impractical, if not impossible, without machine and/or computer support.

Referring next to FIG. 8, an exemplary device X profile 800 and an exemplary device Y profile 802 for a second analysis comparing two devices 204 is shown.

As shown in FIG. 8, each of the two profiles 800, 802 have the same subject: subject A. The difference between the two profiles 800, 802 is the neurotechnology device 204: in the first profile 800, subject A is using device "X". In the second profile 802, subject A is using device "Y". The result using the previously described method and system results in the device utility for device X and the device utility for device Y, as shown in FIGS. 8 and 9.

Returning to the embodiment in which the method of determining which biomedical intervention and/or neurotechnology device among an array of biomedical interventions and/or neurotechnology devices most improves or otherwise impacts a person's ability to perform a cognitively-demanding functional task (such as an Air Traffic controller work sample), assuming that data generation and collection have been completed according to user preferences, the data regarding the two different devices is analyzed and interpreted, and profiles are generated, using the system and method described herein. The results are shown in FIGS. 8 and 9.

The Absolute Performance score 402 for device X is 77 and for device Y is 75. In determining the Absolute Performance score 402, as all subjects' performance rate and quality have been compared to a threshold performance standard, the Absolute Performance score 402 is a criterion-referenced score. In example of FIGS. 7 and 8, Absolute Performance score 402 and Absolute Efficiency score 408 are again not included in the total composite scores 416, but are reported as distinct values, illustrating the invention's inherent capacity to accommodate the user's particular form of tailored interface.

The Relative Performance score 404 for device X is 113 ($81^{th}$ percentile), and for device Y is 91 ($27^{th}$ percentile).

The Relative Effort score 406 for device X is 96 ($40^{th}$ percentile), and for device Y is 103 ($58^{th}$ percentile). Prior to the psychometric analysis, raw data values are inverted in order to ensure that higher standard score values correspond with lower effort exertion.

The Absolute Efficiency score 408 for device X is 1.25 and for device Y is 1.75. For the given Air Traffic Controller work sample, raw performance scores are divided by raw effort scores. As with Absolute Performance score 402, in this example the Absolute Efficiency scores 408 are not included in the Composite score 416.

The Relative Efficiency score 410 for device X is 80 ($9^{th}$ percentile), and for device Y is 117 ($87^{th}$ percentile). As with the Relative Effort score 406, prior to the psychometric analysis, raw data values are inverted in order to ensure that higher standard score values correspond with lower effort exertion.

The Resource Efficiency score 412 for device X is 76 ($5^{th}$ percentile), and for device Y is 130 ($98^{th}$ percentile). As with the Relative Effort score 406, prior to the psychometric analysis, raw data values are inverted in order to ensure that higher standard score values correspond with lower effort exertion.

The Behavioral Efficiency score 414 for device X is 88 ($21^{th}$ percentile), and for device Y is 112 ($79^{th}$ percentile). As with the Relative Effort score 406, prior to the psychometric analysis, raw data values are inverted in order to ensure that higher standard score values correspond with lower effort exertion.

Referring next to FIG. 9, an exemplary device X composite profile 900 and an exemplary device Y composite profile 902 for the second analysis comparing two devices 204 is shown.

In the composite profiles 900, 902 of the second example, the Absolute Performance scores 402 and Absolute Efficiency scores 408 of FIG. 7 are repeated. Also included is the Composite Score 416: for device X, 86 ($18^{th}$ percentile) and for device Y, 115 ($84^{th}$ percentile).

Referring again to FIGS. 8 and 9, by employing the present invention's novel system and method, in which the same single subject performs the same functional activities while using different biomedical interventions and/or neurotechnology devices, the efficacy and the effectiveness, as well as the recommendations for use, of different biomedical interventions and/or neurotechnology devices are assessed and compared using objective representations. Additionally, the complex and multidimensional constructs resulting from the introduction of different biomedical interventions and/or neurotechnology devices are simplified into data sets that facilitate a direct comparison between device X and device Y.

For example, the present embodiment enables the user to identify the impact that using device X has on subject A's performance capacity as compared to when using device Y. When using device Y, subject A exhibits improved effort and efficiency as compared to when using device X; that is, as indicated by the better Relative Effort score 406, when using device Y, subject A exerts less cognitive effort than when completing the same task while using device X. Additionally, as exhibited by the better Relative Efficiency score 410, when using device Y, subject A is able to complete the same task while exerting less cognitive effort in order to achieve the same performance score as his/her age/sex/etc.-matched peers than when using device X. Furthermore, subject A's better Resource Efficiency score 412 when using device Y as compared to when using device X indicates that device Y has enabled subject A to rely on assistive-technology/external-supports less than when using device X. Likewise, subject A's better Behavioral Efficiency score 414 when using device Y as compared to when using device X indicates that device Y has enabled subject A to rely less on compensatory strategies in order to complete the work sample than when using device X. The composite scores 416 reflects the overall superiority of device Y as compared to device X for improving human performance capacity as characterized by performance score versus the investment/usage of resources.

As will be appreciated by one of ordinary skill in the art, given the infinite variety of potential neurotechnology devices and of user preferences, the system and method can be utilized in order to examine an infinite variety of interrelationships among data sets according to the user's specific investigative goals. For example, a user may wish to analyze the affect that using a direct, invasive/non-invasive brain support such as transcranial direct-current stimulation has on a subject's work-sample performance score as well as on a subject's degree and/or frequency of usage of adaptively automated computer workflow-management software designed to mitigate task demands. Alternatively, a user may wish to analyze the affect that using an adaptively automated computer workflow-management software designed to mitigate task demands has on a subject's work-sample performance score as well as on a subject's cognitive effort exertion, usage of direct, invasive/non-invasive brain support such as transcranial direct-current stimulation, or compensatory behavior. As stated above, the infinite variety of interrelationships among data sets will be investigated according to user preferences.

The user of the system and method can determine which biomedical intervention and/or neurotechnology device most improves or otherwise impacts human performance capacity, enabling the fine tuning, altering, adjustment or selection of a given biomedical intervention and/or neurotechnology device based on the impact that the device's usage has on human performance capacity. Results will inform research, development, and marketing programs.

The above descriptions and embodiments enable a person skilled in the art to utilize the present embodiment to assess human performance capacity, and to determine the efficacy and the effectiveness, as well as the recommendations for use, of a given biomedical intervention and/or neurotechnology device to characterize, to predict, and to influence human performance capacity. Principles of data collection, data analysis and interpretation, and profile generation described herein can be applied to a myriad of embodiments while remaining within the spirit and the scope of the present invention.

While the invention herein disclosed has been described by means of specific embodiments, examples and applications thereof, numerous modifications and variations could be made thereto by those skilled in the art without departing from the scope of the invention set forth in the claims.

What is claimed is:

1. A method for evaluating a person-utilized device comprising:
    providing a physical assessment sensor configured to conduct physiological monitoring of a person, collect psychophysiological biomarkers associated with cognitive workload of the person, generate data in response to the monitoring, and send data to an external source;
    performing, by the person, of a standardized work sample while the person is utilizing the person-utilized device and while the person is monitored by the physical assessment sensor, wherein the work sample performance includes the person performing a standardized work sample task, wherein the work sample is associated with a criterion-referenced performance standard, while the person is interacting with at least one work sample object associated with the standardized work sample task during performing of the work sample;
    generating, in response to the performing, of data measuring performance of the person during the performing of the standardized work sample;
    generating, by the physical assessment sensor, in response to the performing, of data measuring cognitive workload of the person during the performing of the standardized work sample, wherein the data measuring cognitive workload comprises collecting of the psychophysiological biomarkers associated with cognitive workload;
    sending of the generated data to a processing device configured to receive, store and process received data;
    generating, by the processing device after completion of the standardized work sample, of an Absolute Performance data set including a comparison of the performance data with the performance standard;
    generating, by the processing device after completion of the standardized work sample, one or more data sets as a function of the data measuring the performance and the data measuring the cognitive workload, the one or more data sets comprising an absolute efficiency data set, wherein the absolute efficiency data set includes a comparison of the Absolute Performance data set to the cognitive workload data;
    generating, by the processing device, an absolute efficiency score based on at least the absolute efficiency data set;
    generating, by the processing device, a composite score as a function of at least the absolute efficiency score;
    generating, by the processing device, a profile of the person's work capacity, the profile including the composite score, wherein the profile indicates the utility of the person-utilized device for the person; and
    performing an evaluation selected from the group of comparing the person-utilized device to at least one other person-utilized device and selecting one person-utilized device based on the comparing, and adjusting the person-utilized device as a function of the profile having been generated to adjust the impact the person-utilized device's usage has on human performance capacity.

2. The method for evaluating the person-utilized device of claim 1 wherein the work sample is associated with norm-referenced performance data measuring generated by other persons performing other work samples, wherein the other work samples are comparable to the work sample and wherein said generating said data sets comprises the step of:
    generating, by the processing device after completion of the standardized work sample, of a Relative Performance data set wherein the Relative Performance data set includes a comparison of the data measuring the performance during the work sample with the norm-referenced performance data wherein the other persons are matched to the person by at least one parameter.

3. The method for evaluating the person-utilized device of claim 1 wherein said generating said data sets comprises the step of:
    generating, by the processing device after completion of the standardized work sample, of a Relative Effort data set wherein the Relative Effort data set includes a comparison of the data measuring the cognitive workload during the work sample with cognitive workload data generated by other persons performing other work samples, wherein the other work samples are comparable to the work sample and the other persons are matched to the person by at least one parameter.

4. The method for evaluating the person-utilized device of claim 1 wherein said generating said data sets comprises the step of:
    generating, by the processing device after completion of the standardized work sample, of a Relative Efficiency data set wherein the Relative Efficiency data set includes a comparison of the data measuring performance and the data measuring cognitive workload, with cognitive workload data and performance data generated by other persons performing other work samples, wherein the other work samples are comparable to the work sample and the other persons are matched to the person by at least one parameter.

5. The method for evaluating the person-utilized device of claim 4 wherein said generating said data sets comprises the steps of:
generating, by the processing device in response of the performing, of data measuring an amount of external supportive resources used by the person during the work sample;
generating, by the processing device after completion of the standardized work sample, of a Resource Efficiency data set wherein the Resource Efficiency data set includes a comparison of a Relative Efficiency score determined from the Relative Efficiency data set with the amount of external supportive resources used by the person during the work sample.

6. The method for evaluating the person-utilized device of claim 4 wherein said generating said data sets comprises the steps of:
generating, in response to the performing, of data measuring an amount of compensatory strategies used by the person during the work sample;
generating, by the processing device after completion of the standardized work sample, of a Behavioral Efficiency data set wherein the Behavioral Efficiency data set includes a comparison of a Relative Efficiency score determined from the Relative Efficiency data set with the amount of compensatory strategies adopted by the person during the work sample.

7. The method for evaluating the person-utilized device of claim 1, further comprising the step of generating measurement of assistive technology assistance utilized by the person while interacting with the physical assessment sensor.

8. The method for evaluating the person-utilized device of claim 7 wherein said measure of assistive technology assistance is independent of said cognitive workload.

9. The method for evaluating the person-utilized device of claim 7, further comprising the step of generating a measurement of compensatory behavior by the person while interacting with the physical assessment sensor.

10. The method for evaluating the person-utilized device of claim 9 wherein said measurement of compensatory behavior is independent of at least one of said measure of assistive technology assistance and said cognitive workload.

11. The method for evaluating the person-utilized device of claim 9, wherein the data sets are generated as a function of the measurement of assistive technology assistance and the measure of compensatory behavior.

12. The method for evaluating the person-utilized device of claim 1, further comprising the step of generating, by the physical assessment sensor, a measurement of compensatory behavior by the person while interacting with the physical assessment sensor.

13. The method for evaluating the person-utilized device of claim 12 wherein said measurement of compensatory behavior is independent of said performance.

14. The method for evaluating the person-utilized device of claim 1, wherein generating said composite score comprises performing a mathematical function on one or more of the one or more data sets.

15. The method for evaluating the person-utilized device of claim 1, wherein said performance of said person is relative to peer performance.

16. The method for evaluating the person-utilized device of claim 1, wherein the person-utilized device is a neurotechnology device.

17. An apparatus for evaluating a person-utilized device comprising:
a physical assessment sensor configured to conduct physiological monitoring of a person, collect psychophysiological biomarkers associated with cognitive workload of the person, generate data in response to the monitoring, and send data to an external source;
a performance measuring system, wherein the performance measuring system is configured to measure performance of the person while monitored by the physical assessment sensor and using the person-utilized device during a standardized work sample task, wherein the work sample is associated with a criterion-referenced performance standard, wherein the person interacts with at least one work sample object associated with the standardized work sample task during the work sample task, the performance measuring system further configured to generate measuring system performance data and send the measuring system performance data to a processing device;
a cognitive workload measuring system, wherein the cognitive workload measuring system is configured to measure psychophysiological biomarkers associated with cognitive workload of the person while monitored by the physical assessment sensor and using the person-utilized device during the standardized work sample task, the cognitive workload measuring system further configured to generate cognitive workload data and send the cognitive workload data to a database;
a processing device configured to process, receive and store data from the performance measuring system and the cognitive workload system, wherein the processing device is configured to:
generate, after completion of the standardized work sample task, an Absolute Performance data set including a comparison of performance data with the performance standard, the performance data including the measuring system performance data;
compile, after completion of the standardized work sample task, one or more data sets as a function of cognitive workload data and the performance data, the one or more data sets comprising an Absolute Efficiency data set wherein the Absolute Efficiency data set includes a comparison of the Absolute Performance data set to the cognitive workload data; and
generate an Absolute Efficiency score based on at least the Absolute Efficiency data set;
a composite score generator of the processing device, wherein the composite score generator is configured to receive receives the one or more data sets and generates in response generate a composite score as a function of at least the absolute efficiency score; and
a profile generator of the processing device, wherein the profile generator receives is configured to receive the one or more data sets and the composite scores and in response generates generate a profile of the person's work capacity, the profile including the composite score, wherein the profile indicates the utility of the person-utilized device for the person, wherein the neurotechnology device is evaluated as a function of the profile having been generated to perform an action selected from the group of comparing the person-utilized device to at least one other person-utilized device and selecting one person-utilized device based on the comparing, and adjusting the person-utilized device as a function of the profile having been generated to adjust the impact the person-utilized device's usage has on human performance capacity.

18. The apparatus for evaluating the person-utilized device of claim 17 wherein the work sample is associated with norm-referenced performance data measuring generated by other persons performing other work samples, wherein the other work samples are comparable to the work sample and wherein the one or more data sets includes a Relative Performance data set wherein the Relative Performance data set includes a comparison of the measured performance during the work sample with the norm-referenced performance data wherein the other persons are matched to the person by at least one parameter.

19. The apparatus for evaluating the person-utilized device of claim 17 wherein the one or more data sets includes a Relative Effort data set wherein the Relative Effort data set includes a comparison of the measured cognitive workload during the work sample with cognitive workload data generated by other persons performing other work samples, wherein the other work samples are comparable to the work sample and the other persons are matched to the person by at least one parameter.

20. The apparatus for evaluating the person-utilized device of claim 17 wherein the one or more data sets includes a Relative Efficiency data set wherein the Relative Efficiency data set includes a comparison of the measured performance and the measured cognitive workload with cognitive workload data and performance data generated by other persons performing other work samples, wherein the other work samples are comparable to the work sample and the other persons are matched to the person by at least one parameter.

21. The apparatus for evaluating the person-utilized device of claim 20 wherein the physical assessment is configured to measure amounts of external supportive resources used by the person during the work sample and the one or more data sets includes a Resource Efficiency data set wherein the Resource Efficiency data set includes a comparison of a Relative Efficiency score determined from the Relative Efficiency data set with the amount of external supportive resources used by the person during the work sample.

22. The apparatus for evaluating the person-utilized device of claim 20 wherein the physical assessment is configured to measure amounts of compensatory strategies used by the person during the work sample and the one or more data sets includes a Behavioral Efficiency data set wherein the Behavioral Efficiency data set includes a comparison of a Relative Efficiency score determined from the Relative Efficiency data set with an amount of compensatory strategies adopted by the person during the work sample.

23. The apparatus for evaluating the person-utilized device of claim 17 further comprising an assistive technology assistance measuring system, wherein the assistive technology assistance measuring system measures assistive technology assistance utilized by the person while interacting with the physical assessment sensor.

24. The apparatus for evaluating the person-utilized device of claim 23 wherein the processing device is configured to receive the measurements of the assistive technology assistance from the assistive technology measuring system and compile one or more data sets as a function of the measure of assistive technology.

25. The apparatus for evaluating the person-utilized device of claim 17 further comprising a compensatory behavior measuring system, wherein the compensatory behavior measuring system measures compensatory behavior by the person while interacting with the physical assessment sensor.

26. The apparatus for evaluating the person-utilized device of claim 25 wherein the processing device is configured to receive the measurements of the compensatory behavior from the compensatory behavior measuring system and compile one or more data sets as a function of the measure of compensatory behavior.

27. The apparatus for evaluating the person-utilized device of claim 17 wherein the person-utilized device is a neurotechnology device.

\* \* \* \* \*

UNITED STATES PATENT AND TRADEMARK OFFICE
CERTIFICATE OF CORRECTION

| | | |
|---|---|---|
| PATENT NO. | : 10,925,533 B2 | Page 1 of 1 |
| APPLICATION NO. | : 16/832206 | |
| DATED | : February 23, 2021 | |
| INVENTOR(S) | : Bruno | |

It is certified that error appears in the above-identified patent and that said Letters Patent is hereby corrected as shown below:

In the Claims
Claim 17, Column 26, Line 53, delete "receive receives" and insert --receive--.
Claim 17, Column 26, Line 53, delete "generates".
Claim 17, Column 26, Line 57, delete "receives".
Claim 17, Column 26, Line 59, delete "generates generate" and insert --generates--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*